(12) United States Patent
Mallalieu et al.

(10) Patent No.: US 11,801,234 B2
(45) Date of Patent: *Oct. 31, 2023

(54) METHODS OF TREATING APOL-1 DEPENDENT FOCAL SEGMENTAL GLOMERULOSCLEROSIS

(71) Applicant: Vertex Pharmaceuticals Incorporated, Boston, MA (US)

(72) Inventors: Navita Mallalieu, Montclair, NJ (US); Ifeatu Egbuna, Hopkinton, MA (US); Brian J. Hare, Arlington, MA (US); Alexander Wolfgang Krug, Needham, MA (US); Shu-Pei Wu, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 260 days.

This patent is subject to a terminal disclaimer.

(21) Appl. No.: 17/193,410

(22) Filed: Mar. 5, 2021

(65) Prior Publication Data

US 2021/0275496 A1    Sep. 9, 2021

Related U.S. Application Data

(60) Provisional application No. 62/986,096, filed on Mar. 6, 2020.

(51) Int. Cl.
| | | |
|---|---|---|
| A61K 31/404 | (2006.01) | |
| A61P 13/12 | (2006.01) | |
| A61K 9/00 | (2006.01) | |
| A61K 9/20 | (2006.01) | |
| A61K 31/573 | (2006.01) | |
| A61K 45/06 | (2006.01) | |

(52) U.S. Cl.
CPC .......... *A61K 31/404* (2013.01); *A61K 9/0053* (2013.01); *A61K 9/2013* (2013.01); *A61K 9/2054* (2013.01); *A61K 31/573* (2013.01); *A61K 45/06* (2013.01); *A61P 13/12* (2018.01); *C07B 2200/13* (2013.01)

(58) Field of Classification Search
CPC .. A61K 31/404; A61K 9/0053; A61K 9/2013; A61K 9/2054; A61K 31/573; A61K 45/06; A61K 9/2077; A61K 9/2853; A61K 31/4045; A61K 2300/00; A61K 9/2813; A61K 9/284; A61P 13/12; C07B 2200/13

See application file for complete search history.

(56) References Cited

U.S. PATENT DOCUMENTS

| | | |
|---|---|---|
| 6,605,633 B1 | 8/2003 | Paquet et al. |
| 2004/0138287 A1 | 7/2004 | Barth et al. |
| 2005/0100902 A1 | 5/2005 | Barth et al. |
| 2013/0237532 A1 | 9/2013 | Kim et al. |
| 2015/0297598 A1* | 10/2015 | Friedman ............. A61K 31/519 |
| 2018/0118681 A1 | 5/2018 | Ross et al. |
| 2021/0246121 A1 | 8/2021 | Lai et al. |
| 2021/0275496 A1 | 9/2021 | Mallalieu et al. |
| 2022/0106327 A1 | 10/2022 | Ahn et al. |
| 2022/0340523 A1 | 10/2022 | Dakin et al. |
| 2023/0011118 A1 | 1/2023 | Dakin et al. |
| 2023/0014907 A1 | 1/2023 | Dakin et al. |

FOREIGN PATENT DOCUMENTS

| | | |
|---|---|---|
| WO | WO 2001/017965 A2 | 3/2001 |
| WO | WO 2001/038305 A2 | 5/2001 |
| WO | WO 2002/028831 A1 | 4/2002 |
| WO | WO 2002/092568 A1 | 11/2002 |

(Continued)

OTHER PUBLICATIONS

Takasawa, R. et al., "Discovery of a new type inhibitor of human glyoxalase I by myricetin-base 4-point pharmacophore," *Biorganic & Medicinal Chemistry Letters*, Pergamon, Amsterdam, NL, vol. 21, No. 14, May 16, 2011, pp. 4337-4342.

(Continued)

*Primary Examiner* — Joseph K McKane
*Assistant Examiner* — David M Shim
(74) *Attorney, Agent, or Firm* — Finnegan, Henderson, Farabow, Garrett & Dunner, LLP

(57) ABSTRACT

This application describes methods of inhibiting APOL1 and treating APOL1-mediated kidney diseases comprising administering Compound I and/or a pharmaceutically acceptable salt thereof.

Compound I

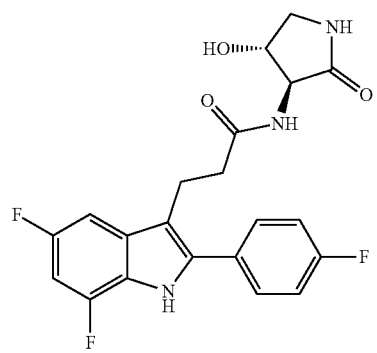

The application also describes pharmaceutical compositions comprising Compound I and/or a pharmaceutically acceptable salt thereof.

38 Claims, 2 Drawing Sheets

(56) References Cited

FOREIGN PATENT DOCUMENTS

| | | |
|---|---|---|
| WO | WO 2003/104180 A1 | 12/2003 |
| WO | WO 2005/092854 A1 | 10/2005 |
| WO | WO 2008/092231 A1 | 8/2008 |
| WO | WO 2010/137351 A1 | 12/2010 |
| WO | WO 2012/025155 A1 | 3/2012 |
| WO | WO 2014/085154 A1 | 6/2014 |
| WO | WO 2015/048301 A1 | 4/2015 |
| WO | WO 2016/055517 A1 | 4/2016 |
| WO | WO 2017/033093 A1 | 3/2017 |
| WO | WO 2019/213148 A1 | 11/2019 |
| WO | WO 2020/131807 A1 | 6/2020 |
| WO | WO 2021/154997 A1 | 8/2021 |
| WO | WO 2021/158666 A1 | 8/2021 |
| WO | WO 2021/178768 A1 | 9/2021 |
| WO | WO 2021/224927 A1 | 9/2021 |
| WO | WO 2021/252849 A1 | 12/2021 |
| WO | WO 2021/252859 A1 | 12/2021 |
| WO | WO 2021/252863 A1 | 12/2021 |
| WO | WO 2022/047031 A1 | 3/2022 |
| WO | WO 2023/028237 A1 | 3/2023 |

OTHER PUBLICATIONS

Balasubramanian, M. et al. (1979) "Studies on Conformation: Part X—Addition of Grignard Reagents to 4-Piperidones." *Indian J. Chem.*, vol. 8, May 1, 1970, pp. 420-422.

Bartolucci, S. et al. (2015), "Iridium-Catalyed Direct Synthesis of Tryptamine Derivatives from Indoles: Exploiting N-Protected Amino Alcohols as Alkylating Agents," *J. Org. Chem*, 2015, 80, 3217-3222.

Casy, A.F. et. al. (1976), "Reversed ester analogues of pethidine: isomeric 4-acetoxy-1,2,6-trimethyl-4-phenyrpiperidines." *JPP*, vol. 28, No. 2, pp. 106-110.

Database Registry 2002, Chembridge Corporation: 4-Piperidinol, 4-(2-methoxyphenyl)-1-methyl-2,6-diphenyl-II XP093022694, Database accession No. 471296-86-4 compound with Registry No. 471296-86-4.

Database Registry (2016), Aurora Fine Chemicals: "Piperidine, 4-[(I,3-diethyl-IH-pyrazol-5-yl)methyl]-2, 6-dimethyl," XP093022702, Database accession No. 1993174-76-7 compounds with Registry Nos. 1993174-76-7, 1993166-16-7 and 1993166-02-1.

Database Registry (2018), Aurora Fine Chemicals: "4-Piperidinol, 1,2,6-trimethyl-4-(2-methylphenyl-" XP093022693, Database accession No. 2182802-01-1 compound with Registry No. 2182802-01-1.

Database Registry (2021), "2'-Cyclopropyl-7,8-dihydro-6'-methylspiro [I,6-naphthyridine-5(6H),4'-piperidine]," XP093024331, retrieved from STN Database accession No. 2645191-67-7 abstract.

Database Registry (2021), "2'Cyclopropyl-6,7-dihydro-6,6'-dimethyls piro[I,7-naphthyridine-8(5H),4'-piperidine,]" XP093024335, retrieved from STN Database accession No. 2644543-73-5 abstract.

Database Registry (2021), Anonymous: "Name not yet assigned"XP093024338, retrieved from STN Database accession No. 2642534-36-7 abstract.

Database Registry (2021), Anonymous: "2'-Cyclopropyl-3,4-dihydro-6'-methylspiro [isoquinoline-1(2H),4'-piperidin]-7-ol," XP093024340, retrieved from STN Database accession No. 2631256-91-0 abstract.

Database Registry (2021), Anonymous: "2-Cyclopropyl-7',8'-dihydro-2',6-dimethyl spiro[piperidine-4,5'(3'H)-pyrido[4,3-d]ph rimidin]-4' (6 H')-one", XP093024343, retrieved from STN Database accession No. 2631119-41-8 abstract.

Database Registry (2021), Anonymous: "Name not yet assigned", XP093024344, retrieved from STN Database accession No. 2630494-88-9 abstract.

Database Registry (2021), Anonymous: "2'-Cyclopropyl-6,7-dihydro-6'-methylspiro [I,7-naphthyridine-8(5H),4' piperidine]-6-methanol," XP093024346, retrieved from STN Database accession No. 2626788-69-8 abstract.

Database Registry (2021), Anonymous: "rel-(2'R,6'R)-3,4-Dihydro-7-methoxy-2',6'-dimethylspiro[2,6-naphthyridine1(2H),4'-p iperidine]," XP093024348, retrieved from STN Database accession No. 2625380-27-8 abstract.

Database Registry (2021), Anonymous: "2'-Cyclopropyl-3,4-dihydro-3,6'-dimethyls piro[2,6-naphthyridine-1(2H),4'piperidine]," XP093024352, retrieved from STN Database accession No. 2620609-98-3 abstract.

Database Registry (2021), Anonymous: "2'-Cyclopropyl-6,7-dihydro-6'-methylspiro [I,7-naphthyridine-8(5H),4' piperidine]-5-methanol," XP093024350, retrieved from STN Database accession No. 2617381-98-1 abstract.

Dummer, P.D. et al. (2015), "APOL1 kidney disease risk variants—an evolving landscape," *Semin Nephrol.* 35(3):222-236. HHS Public Access Author Manuscript; available in PMC May 1, 2016 (25 pages).

Harish, B. et al. (2017) "N-Heterocyclic carbene (NHC)-catalysed atom economical construction of 2,3-disubstituted indoles," *Chem. Commun*, 2017, 53, 3338-3341.

Harper N.J. et al. (1960) "Some isomeric hydroxypiperidines." *J. Am. Chem. Soc.*, Jan. 1, 1960, pp. 2704-2711.

International Search Report and Written Opinion for International Application No. PCT/US2021/021037, dated Jul. 5, 2021 (10 pages).

Jones, A.J. et al. (1973), "Carbon-13 Magnetic Resonance: the Stereochemistry of 1,2- and 1,3-Dimethyl-4-phenylpiperidine Derivatives." *Can. J. Chem.*, vol. 41, No. 11, pp. 1782-1789.

Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.

Kozikowski, A.P. et al. (1993), "Chemistry, binding affinities, and behavioral properties of a new class of "antineophobic" mitochondrial DBI receptor complex (mDRC) ligands," *J. Med. Chem.* 36(20):2908-2920.

Lin, J. et al. (2021), "Oncogene APOL1 promotes proliferation and inhibits apoptosis via activating NOTCH1 signaling pathway in pancreatic cancer," *Cell Death and Disease* 12:760 (11 pages).

Manimekalai, A. et al. (2007), "Benzyl group conformation in 4-benzyl-4-hydroxypiperidines," *J. Struct. Chem.*, vol. 48, No. 6, pp. 1036-1045.

Meyers, A.L. et al. (1985), ".alpha.-Amino carbanions. Preparation, metalation, and alkylation of enamidines. Synthesis of piperidine and pyrrolidine natural products and homologation of carbonyl compounds," *J. Org. Chem.*, vol. 50, No. 7, pp. 1019-1026.

Notice of Allowance and Fee(s) Due for U.S. Appl. No. 16/717,099, dated Nov. 7, 2022.

Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.

Trotter, B.W. et al. (2001) "2-Arylindole-3-acetamides: FPP-Competitive Inhibitors of Farnesyl Protein Transferase," Bioorg. Med. Chem. Lett. 11(2001) 865-869.

Turnu, F. et al. (2019) "Catalytic Tandem Friedel—Crafts Alkylation/C4-C3 Ring-Contraction Reaction: An Efficient Route for the Synthesis of Indolyl Cyclopropanecarbaldehydes and Ketones," *Org. Lettl*. 21:7329-7332, (4 pages).

U.S. Appl. No. 17/895,582, filed Aug. 25, 2022, by Daniel et. al.
U.S. Appl. No. 17/923,508, filed Nov. 11, 2022 by Skorecki, et al.
U.S. Appl. No. 18/001,371, filed Dec. 9, 2022 by Gagnon, et al.
U.S. Appl. No. 18/071,153, filed Nov. 29, 2022, by Dakin et. al.

Vajgel, G. et al. (2020), "A single APOL1 nephropathy variant increases risk of advanced lupus nephritis in Brazilians," *J Rheumatol.* 47(8):1209-1217. HHS Public Access Author Manuscript; available in PMC Aug. 1, 2021 (18 pages).

Valles, D.A. et al. (2021), "[alpha], [alpha] '-C—H Bond Difunctionalization of Unprotected Alicyclic Amines," *Org. Lett.*, vol. 23, No. 16, pp. 6367-6371.

*Vertex Announces Positive Results From Phase 2 Study of VX-147 in APOL1-Mediated Focal Segmental Glomerulosolerosis*, Vertex (Dec. 1, 2021), https://news.vnx.com/press-release/venex-announces-positive-results-phase-2-study-vx-147-apol1-mediated-focal-segmental (6 pages).

(56) References Cited

OTHER PUBLICATIONS

Winters, M.P. et al. (2008), "Carboxylic acid bioisosteres acylsulfonamides, acylsulfamides, and sulfonylureas as novel antagonists of the CXCR2 receptor," *Bioorganic Med. Chem. Lett.* 18:1926-1930.

* cited by examiner

METHODS OF TREATING APOL-1 DEPENDENT FOCAL SEGMENTAL GLOMERULOSCLEROSIS

This application claims priority to U.S. Provisional Patent Application 62/986,096, filed Mar. 6, 2020, the contents of which is incorporated by reference in its entirety. This disclosure is directed to methods of treating APOL1-mediated diseases, including APOL1-mediated kidney disease, such as, e.g., APOL1-mediated focal segmental glomerulosclerosis (FSGS) and/or APOL1-mediated non-diabetic kidney disease (NDKD) comprising administering Compound I, a pharmaceutically acceptable salt thereof, and/or a deuterated derivative of Compound I or salt thereof. The disclosure also provides pharmaceutical compositions comprising therapeutic dosages of Compound I, a deuterated derivative of Compound I, and/or pharmaceutically acceptable salt of Compound I or its deuterated derivative.

NDKD is a kidney disease involving damage to the podocyte or glomerular vascular bed that is not attributable to diabetes. FSGS is a rare kidney disease with an estimated global incidence of 0.2 to 1.1/100,000/year. FSGS and NDKD are caused by damage to podocytes, which are part of the glomerular filtration barrier, resulting in proteinuria. Patients with proteinuria are at a higher risk of developing end-stage kidney disease (ESKD) and developing proteinuria-related complications, such as infections or thromboembolic events. There is no standardized treatment regimen nor approved drugs for FSGS or NDKD. Current therapeutic options for patients with FSGS and proteinuria include high-dose corticosteroids, which induce remission of proteinuria in a minority of patients. Current therapeutic options for NDKD are anchored on blood pressure control and blockade of the renin angiotensin system.

FSGS and NDKD can be divided into different subgroups based on the underlying etiology. One homogeneous subgroup of FSGS is characterized by the presence of independent common sequence variants in the apolipoprotein L1 (APOL1) gene termed G1 and G2, which are referred to as the "APOL1 risk alleles." G1 encodes a correlated pair of non-synonymous amino acid changes (S342G and I384M), G2 encodes a 2 amino acid deletion (N388del:Y389del) near the C terminus of the protein, and G0 is the ancestral (low risk) allele. A distinct phenotype of NDKD is found in patients with APOL1 genetic risk variants as well. In both APOL1-mediated FSGS and NDKD, higher levels of proteinuria and a more accelerated loss of kidney function occur in patients with two risk alleles compared to patients with the same disease who have no or just 1 APOL1 genetic risk variant.

The APOL1 gene is expressed in multiple organs in humans, including the liver and kidney. APOL1 protects against parasitic infection by *Trypanosoma brucei brucei* (*T. b. brucei*). APOL1 is endocytosed by *T. b. brucei* and transported to lysosomes, where it inserts into the lysosomal membrane and forms pores that lead to parasite swelling and death. While the ability to lyse *T. b. brucei* is shared by all 3 APOL1 variants (G0, G1, and G2), APOL1 G1 and G2 variants confer additional protection against parasite species that have evolved a serum resistant associated-protein (SRA) which inhibits APOL1 G0; these species cause sleeping sickness. G1 and G2 variants evade inhibition by SRA; G1 confers additional protection against *T. b. gambiense* (which causes West African sleeping sickness) while G2 confers additional protection against *T. b. rhodesiense* (which causes East African sleeping sickness).

In the kidney, APOL1 is expressed in podocytes, endothelial cells (including glomerular endothelial cells), and some tubular cells. Podocyte-specific expression of APOL1 G1 or G2 (but not G0) in transgenic mice induces structural and functional changes, including albuminuria, decreased kidney function, podocyte abnormalities, and glomerulosclerosis. Consistent with these data, G1 and G2 variants of APOL1 play a causative role in inducing FSGS and accelerating its progression in humans. Individuals with APOL1 risk alleles (i.e., homozygous or compound heterozygous for the APOL1 G1 or APOL1 G2 alleles) have increased risk of developing FSGS and they are at risk for rapid decline in kidney function if they develop FSGS. Thus, inhibition of APOL1 could have a positive impact in individuals who harbor APOL1 risk alleles.

3-[5,7-difluoro-2-(4-fluorophenyl)-1H-indol-3-yl]-N-[(3 S,4R)-4-hydroxy-2-oxo-pyrrolidin-3-yl]propanamide (Compound I) is a small molecule inhibitor of APOL1-induced cell death and APOL1-induced lysis of *T. b. brucei*. Compound I can be depicted as having the following structure:

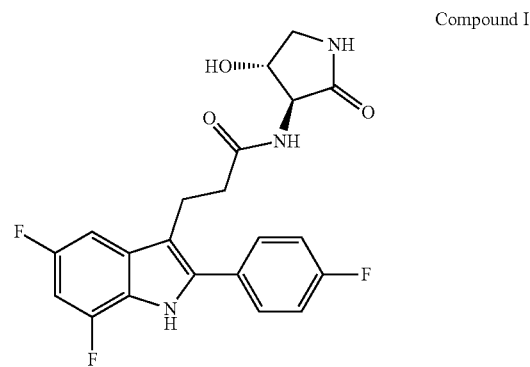 [SMILES: O=C(CCc1c(-c2ccc(F)cc2)[nH]c2c(F)cc(F)cc12)N[C@@H]1C(=O)NC[C@H]1O]

Compound I

Compound I, its method of preparation, and physicochemical data are disclosed (as "Compound 2") in copending U.S. application Ser. No. 16/717,099 and PCT International Application No. PCT/US2019/066746, both of which are incorporated herein by reference for this disclosure.

This disclosure provides methods of inhibiting APOL1-induced cell death and treatment of APOL1-mediated diseases, including APOL1-mediated kidney diseases, such as, e.g., FSGS and/or NDKD by administering a pharmaceutical composition comprising a therapeutically effective amount of Compound I, a deuterated derivative of Compound I, and/or pharmaceutically acceptable salt of Compound I or deuterated derivative of Compound I. The methods and pharmaceutical compositions disclosed herein provide treatment for individuals with APOL1-mediated kidney diseases associated with one or more APOL1 risk alleles and with or without proteinuria (i.e., protein to creatinine ratio >3 g/g for individuals with nephrotic-range proteinuria; protein to creatinine ratio of >0.15 g/g to <3.0 g/g for individuals with sub nephrotic-range proteinuria). The methods and pharmaceutical compositions disclosed herein provide treatment for individuals with APOL1-mediated kidney diseases associated with one or more APOL1 risk alleles, with or without nephrotic-range proteinuria.

In some embodiments, the disclosure relates to pharmaceutical compositions comprising a therapeutically effective amount of Compound I, a deuterated derivative of Compound I, and/or pharmaceutically acceptable salt of Compound I or deuterated derivative of Compound I.

In some embodiments, the disclosure relates to pharmaceutical compositions comprising Compound I, a deuterated derivative of Compound I, and/or pharmaceutically acceptable salt of Compound I or deuterated derivative of Compound I, which compositions may further include at least one additional active pharmaceutical ingredient and/or at least one carrier. In some embodiments, the disclosure provides methods of treating APOL1-mediated kidney disease, including FSGS and/or NDKD comprising administering Compound I, a deuterated derivative of Compound I, and/or pharmaceutically acceptable salt of Compound I or deuterated derivative of Compound I, optionally as part of a pharmaceutical composition comprising at least one additional active component, to a subject in need thereof.

DEFINITIONS

Figure 1:
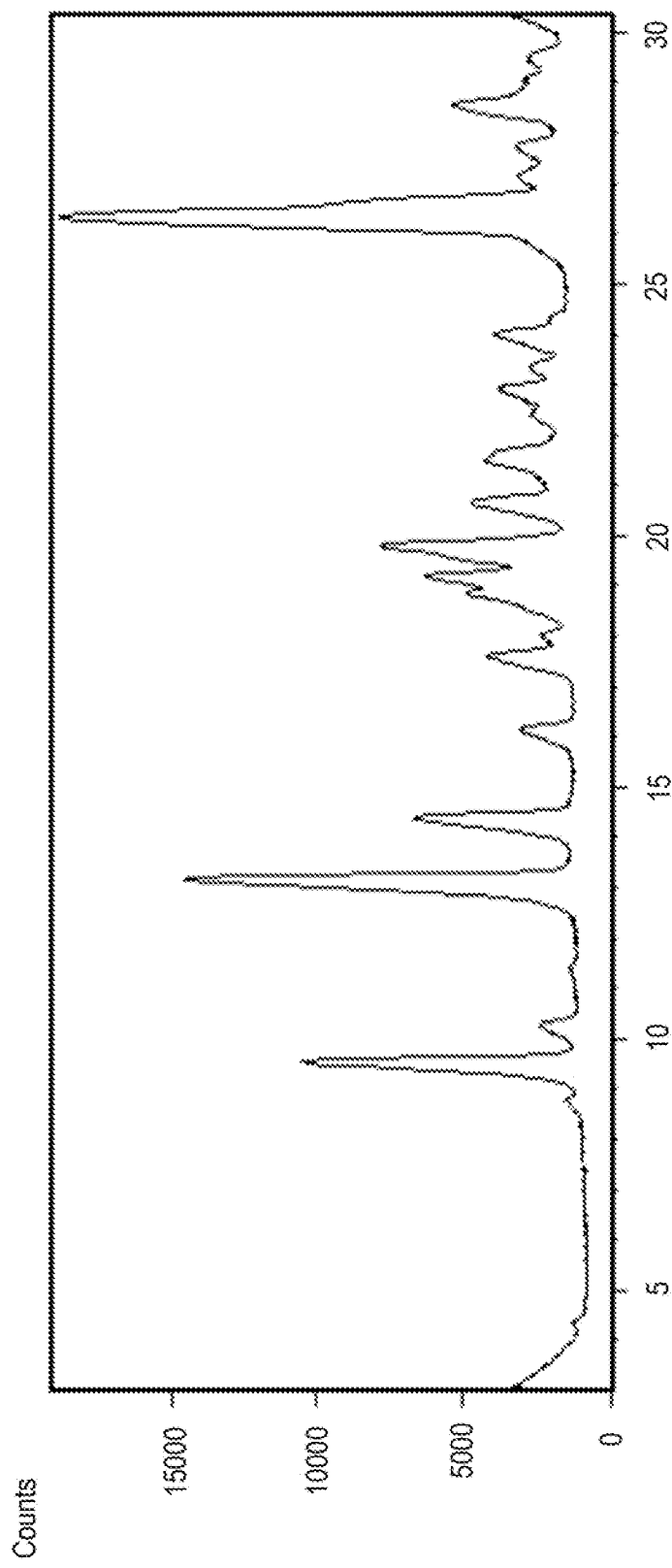
FIG. 1 depicts an XRPD diffractogram of Compound I Form A.

"Compound I" as used throughout this disclosure refers to 3-[5,7-difluoro-2-(4-fluorophenyl)-1H-indol-3-yl]-N-[(3 S,4R)-4-hydroxy-2-oxo-pyrrolidin-3-yl]propanamide, which can be depicted as having the following structure:

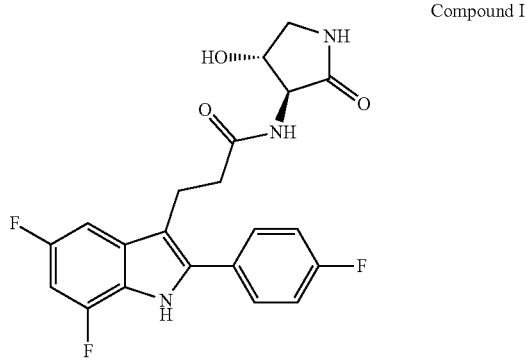 [SMILES: O=C(CCc1c(-c2ccc(F)cc2)[nH]c2c(F)cc(F)cc12)N[C@@H]1C(=O)NC[C@H]1O]

Compound I

Compound I may be in the form of a deuterated derivative, or a pharmaceutically acceptable salt of the compound or deuterated derivative. In some embodiments, Compound I is administered in crystalline or substantially pure crystalline Form A.

The term "APOL1" as used herein means apolipoprotein L1 protein and the term "APOL1" means apolipoprotein L1 gene.

The term "FSGS" as used herein means focal segmental glomerulosclerosis, which is a disease of the podocyte (glomerular visceral epithelial cells) responsible for proteinuria and progressive decline in kidney function, and associated with 2 common APOL1 genetic variants (G1: S342G: I384M and G2: N388del:Y389del).

The term "NDKD" as used herein means non-diabetic kidney disease, which is a kidney disease involving damage to the podocyte or glomerular vascular bed that is not attributable to diabetes, and is associated with 2 common APOL1 genetic variants (G1: S342G:I384M and G2: N388del:Y389del). This includes but is not limited to hypertensive kidney disease, lupus, minimal change, membranous nephropathy, steroid resistant or steroid sensitive nephrotic syndrome and renal allograft dysfunction. In some embodiments, it includes chronic kidney disease in non-diabetic patients with hypertension and proteinuria ≥0.2 g/g but not chronic kidney disease caused by infection, malignancy, obstruction or autoimmune disorders.

The terms "patient" and "subject" are used interchangeably and refer to an animal including a human.

As used herein, the terms "treatment," "treating," and the like generally mean the improvement of APOL1-mediated diseases, including APOL1-mediated kidney diseases, such as but not limited FSGS and/or NDKD or one or more of symptoms and/or lessening the severity of FSGS and/or NDKD or one or more of its symptoms in a subject. "Treatment" and its cognates, as used herein, include, but are not limited to the following: complete or partial remission, lower risk of kidney failure (e.g. ESRD), and disease-related complications (e.g. edema, susceptibility to infections, or thrombo-embolic events). Improvements in or lessening the severity of any of these symptoms can be readily assessed according to methods and techniques known in the art or subsequently developed.

As used herein, a "therapeutically effective" amount of Compound I refers to that amount of Compound I, a deuterated derivative of Compound 1, or a pharmaceutically acceptable salt of Compound I or its deuterated derivative that produces the desired effect for which it is administered (e.g., improvement in symptoms of an APOL1-mediated kidney disease, lessening the severity of an APOL1-mediated kidney disease or a symptom of an APOL1-mediated kidney disease, and/or reducing progression of an APOL1-mediated kidney disease or a symptom of an APOL1-mediated kidney disease, improvement in symptoms of FSGS and/or NDKD, lessening the severity of FSGS and/NDKD or a symptom of FSGS and/or NDKD, and/or slowing or reducing progression of FSGS and/or NDKD or a symptom of FSGS and/or NDKD). The exact amount of a therapeutically effective dose will depend on the purpose of the treatment and will be ascertainable by one skilled in the art using known techniques (see, e.g., Lloyd (1999) The Art, Science and Technology of Pharmaceutical Compounding). In some embodiments, the therapeutically effective dose of Compound I is 2 mg to 250 mg. Other suitable therapeutically effective doses are disclosed herein.

As used herein, "ULN" means "upper limit of normal."

As used herein, the term "in combination with," when referring to two or more compounds, agents, or additional active pharmaceutical ingredients, means the administration of two or more compounds, agents, or active pharmaceutical ingredients to the patient prior to, concurrently with, or subsequent to each other.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction and solid state nuclear magnetic resonance (SSNMR). Accordingly, as used herein, the term "crystalline Form A of Compound I" refers to a unique crystalline form that can be identified and distinguished from other forms by any one or more characterization techniques including, for example, XRPD, single crystal X-ray diffraction, and SSNMR. In some embodiments, the Compound I crystalline Form A is characterized by an X-ray powder diffractogram having one or more signals at one or more specified two-theta values (° 2θ).

As used herein, the term "SSNMR" refers to the analytical characterization method of solid state nuclear magnetic resonance. SSNMR spectra can be recorded at ambient conditions on any magnetically active isotope present in the sample. The typical examples of active isotopes for small molecule active pharmaceutical ingredients include $^{1}H$, $^{2}H$, $^{13}C$, $^{19}F$, $^{31}P$, $^{15}N$, $^{14}N$, $^{35}Cl$, $^{11}B$, $^{7}Li$, $^{17}O$, $^{23}Na$, $^{79}Br$, and $^{195}Pt$.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [α] two-theta value(s) of . . . " and/or "a signal at at least . . . two-theta value(s) chosen from . . . ."

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [α] two-theta value[ ] of . . . " and/or "a signal at at least . . . two-theta value(s) chosen from . . . " refer to X-ray reflection positions as measured and observed in X-ray powder diffraction experiments (° 2θ).

The repeatability of the angular values is in the range of ±0.2° 2θ, i.e., the angular value can be at the recited angular value+0.2 degrees two-theta, the angular value −0.2 degrees two-theta, or any value between those two end points (angular value+0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The term "X-ray powder diffractogram having a signal at . . . two-theta values" as used herein refers to an XRPD pattern that contains X-ray reflection positions as measured and observed in X-ray powder diffraction experiments (° 2θ).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal maximum values in SSNMR spectra (in ppm) referred to herein generally mean that value reported ±0.2 ppm of the reported value, an art-recognized variance.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describes pharmaceutically acceptable salts in detail in *J. Pharmaceutical Sciences*, 1977, 66, 1-19.

Suitable pharmaceutically acceptable salts are, for example, those disclosed in S. M. Berge, et al. *J. Pharmaceutical Sciences*, 1977, 66, 1-19. For example, Table 1 of that article reproduced below provides the following pharmaceutically acceptable salts.

TABLE 1

Exemplary Pharmaceutically Acceptable Salts

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}$ alkyl$)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, a "deuterated derivative of Compound I" refers to a form of Compound I in which at least one hydrogen has been replaced by a deuterium atom. It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at least 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

In some embodiments, the disclosure is also directed to methods of treatment using isotope-labelled compound of Compound I, which, in some embodiments, are referred to as Compound I or pharmaceutically acceptable salt(s) thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^3H$)- and/or carbon-14 ($^{14}C$)-labelled compounds are particularly useful for various types of assays, such as substrate tissue distribution assays, due to relatively simple preparation and excellent detectability. For example, deuterium ($^2H$)-labelled ones are therapeutically useful with potential therapeutic advantages over the non-$^2H$-labelled compounds. In general, deuterium ($^2H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2H$)-labelled ones. In some specific embodiments, the isotope-labelled compounds and salts are deuterium ($^2H$)-labelled, wherein one or more hydrogen atoms therein have been replaced by deuterium. In chemical structures, deuterium is represented as "D."

The deuterium ($^2H$)-labelled compounds and salts can experience an altered rate of oxidative metabolism relative to the non-deuterium ($^2$H)-labelled compound or salt by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For example, if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range.

One of ordinary skill in the art would recognize that, when an amount of "a compound or a deuterated derivative thereof or a pharmaceutically acceptable salt of the compound or deuterated derivative thereof" is disclosed, the amount of the pharmaceutically acceptable salt form of the compound is the amount equivalent to the concentration of the free base of the compound or deuterated derivative thereof. It is noted that the disclosed amounts of the compounds or their pharmaceutically acceptable salts thereof herein are based upon their free base form. For example, "100 mg of at least one compound chosen from Compound I and pharmaceutically acceptable salts thereof" includes 100 mg of Compound I and a concentration of a pharmaceutically acceptable salt of Compound I equivalent to 100 mg of Compound I.

As used herein, administration of a "daily" amount of Compound I, or a deuterated derivative or a pharmaceutically acceptable salt thereof refers to the total amount that is administered in one day but does not limit the frequency of administration per day. The daily amount administered to a patient can be administered once or multiple times in a day, such as twice daily or three times daily (wherein each of multiple administrations comprises administering some amount of Compound I or a deuterated derivative or pharmaceutically acceptable salt thereof that is less than the "daily" amount, given that the "daily" amount refers to the total amount administered in one day). Each administration of Compound I or a deuterated derivative or pharmaceutically acceptable salt thereof can consist of administering Compound I or a deuterated derivative or pharmaceutically acceptable salt thereof in the form of a single composition (e.g., a single dosage, such as a single tablet or a single capsule) or in the form of multiple compositions (e.g., multiple dosages, such as multiple (i.e., two or more) tablets and/or capsules).

In some embodiments, Compound I used in the methods and compositions of the invention is in crystalline form Form A. In some embodiments, Compound I is in substantially pure crystalline Form A. In some embodiments, Compound I Form A is characterized by an X-ray powder diffractogram substantially similar to that in FIG. 1. In some embodiments, Compound I Form A is characterized by an X-ray powder diffractogram having a signal at at least two two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least three two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least four two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least five two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least six two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least seven two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at at least eight two-theta values chosen from 9.5±0.2, 13.2±0.2, 14.4±0.2, 19.2±0.2, 19.5±0.2, 19.8±0.2, 26.3±0.2, 26.7±0.2, and 28.6±0.2. In some embodiments, Compound I Form A is characterized by an X-ray powder diffractogram having a signal at the following two-theta values 9.5±0.2, 13.2±0.2, 14.4±0.2, 19.2±0.2, 19.5±0.2, 19.8±0.2, 26.3±0.2, 26.7±0.2, and 28.6±0.2.

In some embodiments, Compound I Form A used in the methods and compositions of the invention is characterized by an X-ray powder diffractogram having a signal at at least one two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Compound I Form A is characterized by an X-ray powder diffractogram having a signal at at least two two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Compound I Form A is characterized by an X-ray powder diffractogram having a signal at at least three two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Compound I Form A is characterized by an X-ray powder diffractogram having a signal at at least four two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, 28.6±0.2, 29.1±0.2, and 29.5±0.2. In some embodiments, Compound I Form A is characterized by an X-ray powder diffractogram having a signal at at least five two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Compound I Form A is characterized by an X-ray powder diffractogram having a signal at at least six two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Compound I Form A is characterized by an X-ray powder diffractogram having a signal at at least seven two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Compound I Form A is characterized by an X-ray powder diffractogram having a signal at at least eight two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Compound I Form A is characterized by an X-ray powder diffractogram having a signal at at least nine two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2. In some embodiments, Compound I Form A is characterized by an X-ray powder diffractogram having a signal at at least ten two-theta values chosen from 9.5±0.2, 13.2±0.2, 14.4±0.2, 16.1±0.2, 17.7±0.2, 18.8±0.2, 19.2±0.2, 19.5±0.2, 19.8±0.2, 20.7±0.2, 21.4±0.2, 21.7±0.2, 22.4±0.2, 22.9±0.2, 23.3±0.2, 24.0±0.2, 26.3±0.2, 26.7±0.2, 27.1±0.2, 27.7±0.2, and 28.6±0.2.

In some embodiments, Compound I used in the methods and compositions of the invention is Compound I Form A. In some embodiments, Compound I used in the methods and compositions of the invention is substantially pure Form A.

In some embodiments, Compound I Form A used in the methods and compositions of the invention is characterized by a $^{13}$C NMR spectrum having a signal at at least one ppm value chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Compound I Form A is characterized by a $^{13}$C NMR spectrum having a signal at at least two ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Compound I Form A is characterized by a $^{13}$C NMR spectrum having a signal at at least three ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Compound I Form A is characterized by a $^{13}$C NMR spectrum having a signal at at least four ppm values chosen from 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm. In some embodiments, Compound I Form A is characterized by a $^{13}$C NMR spectrum having a signal at 178.7±0.2 ppm, 154.4±0.2 ppm, 127.8±0.2 ppm, 125.2±0.2 ppm, 102.0±0.2 ppm, 59.3±0.2 ppm, 38.9±0.2 ppm, and 24.4±0.2 ppm.

In some embodiments, Compound I is a substantially crystalline solid. In some embodiments, the crystalline solid consists of 75% to 99% Form A relative to the total weight of the crystalline solid Compound I. In some embodiments, the crystalline solid consists of 80% to 99% Form A relative to the total weight of the crystalline solid Compound I. In some embodiments, the crystalline solid consists of 85% to 99% Form A relative to the total weight of the crystalline solid Compound I. In some embodiments, the crystalline solid consists of 90% to 99% Form A relative to the total weight of the crystalline solid Compound I. In some embodiments, the crystalline solid consists of 95% to 99% Form A relative to the total weight of the crystalline solid Compound I.

In some embodiments, the disclosure provides methods of treating an APOL1-mediated disease with Compound I, Compound I Form A, a deuterated derivative of Compound I, and/or pharmaceutically acceptable salt of Compound I or its deuterated derivative. In some embodiments, Compound I, Compound I Form A, a deuterated derivative of Compound I, and/or pharmaceutically acceptable salt of Compound I or its deuterated derivative is administered daily. In some embodiments, Compound I, Compound I Form A, a deuterated derivative of Compound I, and/or pharmaceutically acceptable salt of Compound I or its deuterated derivative is administered once daily or multiple times daily, such as twice daily or three times daily. In some embodiments, Compound I, Compound I Form A, a deuterated derivative of Compound I, and/or pharmaceutically acceptable salt of Compound I or its deuterated derivative is administered once daily. In some embodiments, Compound I, Compound I Form A, a deuterated derivative of Compound I, and/or pharmaceutically acceptable salt of Compound I or its deuterated derivative is administered twice daily. In some embodiments, Compound I, Compound I Form A, a deuterated derivative of Compound I, and/or pharmaceutically acceptable salt of Compound I or its deuterated derivative is administered three times daily.

In some embodiments, Compound I, Compound I Form A, a deuterated derivative of Compound I, and/or pharmaceutically acceptable salt of Compound I or its deuterated derivative is administered as a single composition. In some embodiments, Compound I, Compound I Form A, a deuterated derivative of Compound I, and/or a pharmaceutically acceptable salt of Compound I or its deuterated derivative thereof is administered in multiple compositions (for example, as multiple tablets and/or multiple pills per single administration). Accordingly, in some embodiments, Compound I, Compound I Form A, a deuterated derivative of Compound I, and/or a pharmaceutically acceptable salt of Compound I or its deuterated derivative is administered once daily as a single composition. In some embodiments, Compound I, Compound I Form A, a deuterated derivative of Compound I, and/or a pharmaceutically acceptable salt of Compound I or its deuterated derivative is administered once daily as multiple compositions, which are administered contemporaneously.

In some embodiments, a therapeutically effective amount of Compound I, Compound I Form A, a deuterated derivative of Compound I, and/or pharmaceutically acceptable salt of Compound I or its deuterated derivative is administered in a daily dosage of 2 mg to 250 mg, 5 mg to 200 mg, 10 mg to 150 mg, 15 mg to 100 mg, 20 mg to 80 mg, or 25 mg to 75 mg. In certain embodiments, a therapeutically effective amount of Compound I, Compound I Form A, a deuterated derivative of Compound I, and/or pharmaceutically acceptable salt of Compound I or its deuterated derivative is administered in a daily dosage of 15 mg to 30 mg, 15 mg to 45 mg, 15 mg to 60 mg, 15 mg to 75 mg, 30 mg to 45 mg, 30 mg to 60 mg, or 30 mg to 75 mg.

In some embodiments, Compound I, Compound I Form A, a deuterated derivative of Compound I, and/or a pharmaceutically acceptable salt of Compound I or its deuterated derivative is administered once daily, twice daily, or three times daily in total daily amount of 2 mg to 250 mg, 5 mg to 200 mg, 10 mg to 150 mg, 15 mg to 100 mg, 20 mg to 80 mg, 25 to 75 mg, 30 to 60 mg, or 15 mg to 45 mg. In some embodiments, Compound I, Compound I Form A, a deuterated derivative of Compound I, and/or a pharmaceutically acceptable salt of Compound I or its deuterated derivative is administered once daily, twice daily, or three times daily in an amount of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg. In some embodiments, Compound I, Compound I Form A, a deuterated derivative of Compound I, and/or a pharmaceutically acceptable salt of Compound I or its deuterated derivative is administered in a daily amount of 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg once daily. In some embodiments, Compound I, Compound I Form A, a deuterated derivative of Compound I, and/or a pharmaceutically acceptable salt of Compound I or its deuterated derivative is administered twice daily in a daily amount of 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg, i.e., Compound I, Compound I Form A, a deuterated derivative of Compound I, and/or a pharmaceutically acceptable salt of Compound I or its deuterated derivative is administered in a daily amount (i.e., total amount per day) of 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg in two portions (which may be equal or unequal) during a single day. Reference to administration of Compound I, a deuterated derivative of Compound I, and/or a pharmaceutically acceptable salt of Compound I or its deuterated derivative in an amount of "twice daily" refers to administering an amount of Compound I, Compound I Form A, a deuterated derivative or a pharmaceutically acceptable salt thereof, two times in one day, wherein each of the two administrations comprises administration of some amount of Compound I, Compound I Form A, a deuterated derivative of Compound I, and/or a pharmaceutically acceptable salt of Compound I or its deuterated derivative that is less than the daily amount, but where the total of these amounts administered in the one day equals the daily amount.

In some embodiments, Compound I, Compound I Form A, a deuterated derivative of Compound I, and/or a pharmaceutically acceptable salt of Compound I or its deuterated derivative is administered every 8 hours ("q8h"), every 12 hours ("q12h"), or every 24 hours ("q24h"). In some embodiments, Compound I, Compound I Form A, a deuterated derivative of Compound I, and/or a pharmaceutically acceptable salt of Compound I or its deuterated derivative is administered every 8 hours (q8h). In some embodiments, Compound I, Compound I Form A, a deuterated derivative of Compound I, and/or a pharmaceutically acceptable salt of Compound I or its deuterated derivative is administered every 12 hours (q12h). In some embodiments, Compound I, Compound I Form A, a deuterated derivative of Compound I, and/or a pharmaceutically acceptable salt of Compound I or its deuterated derivative is administered every 24 hours (q24h).

In some embodiments, Compound I, Compound I Form A, a deuterated derivative of Compound I, and/or a pharmaceutically acceptable salt of Compound I or its deuterated derivative is administered in an amount of 2 mg, 5 mg, 10 mg, 15 mg, 20 mg, 25 mg, 30 mg, 35 mg, 40 mg, 45 mg, 50 mg, 55 mg, 60 mg, or 75 mg every 12 hours (q12h).

In some embodiments, Compound I, Compound I Form A, a deuterated derivative of Compound I, and/or a pharmaceutically acceptable salt of Compound I or its deuterated derivative is administered in an amount of 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg every 24 hours (q24h). In some embodiments, Compound I, Compound I Form A, a deuterated derivative of Compound I, and/or a pharmaceutically acceptable salt thereof is administered in an amount of 15 mg, 20 mg, 25 mg, 30 mg, 35 mg, 40 mg, 45 mg, 50 mg, 55, mg, 60 mg, 65 mg, 70, mg, 75 mg, or 80 mg every 24 hours (q24h).

In some embodiments, Compound I, a deuterated derivative of Compound I, and/or a pharmaceutically acceptable salt of Compound I or its deuterated derivative is administered in an amount of 15 mg every 24 hours (q24h). In some embodiments, Compound I, a deuterated derivative of Compound I, and/or a pharmaceutically acceptable salt of Compound I or its deuterated derivative is administered in an amount of 30 mg every 24 hours (q24h). In some embodiments, Compound I, a deuterated derivative of Compound I, and/or a pharmaceutically acceptable salt of Compound I or its deuterated derivative is administered in an amount of 45 mg every 24 hours (q24h). In some embodiments, Compound I, a deuterated derivative of Compound I, and/or a pharmaceutically acceptable salt of Compound I or its deuterated derivative is administered in an amount of 60 mg every 24 hours (q24h). In some embodiments, Compound I, a deuterated derivative of Compound I, and/or a pharmaceutically acceptable salt of Compound I or its deuterated derivative is administered in an amount of 75 mg every 24 hours (q24h).

In some embodiments, Compound I Form A is administered in an amount of 15 mg every 24 hours (q24h). In some embodiments, Compound I Form A is administered in an amount of 30 mg every 24 hours (q24h). In some embodiments, Compound I Form A is administered in an amount of 45 mg every 24 hours (q24h). In some embodiments, Compound I Form A is administered in an amount of 60 mg every 24 hours (q24h). In some embodiments, Compound I Form A is administered in an amount of 75 mg every 24 hours (q24h).

In some embodiments, Compound I Form A is administered in an amount of 15 mg to 30 mg every 24 hours (q24h). In some embodiments, Compound I Form A is administered in an amount of 30 mg to 45 mg every 24 hours (q24h). In some embodiments, Compound I Form A is administered in an amount of 45 mg to 60 mg every 24 hours (q24h). In some embodiments, Compound I Form A is administered in an amount of 60 mg to 75 mg every 24 hours (q24h).

In some embodiments, the disclosure provides pharmaceutical compositions comprising Compound I, Compound I Form A, a deuterated derivative of Compound I, and/or a pharmaceutically acceptable salt of Compound I or its deuterated derivative, which compositions may further include at least one additional active pharmaceutical ingredient and/or at least one carrier. In some embodiments, the disclosure provides a pharmaceutical composition comprising at least one compound chosen from Compound I, Compound I Form A, a deuterated derivative of Compound I, and/or a pharmaceutically acceptable salt of Compound I or its deuterated derivative, and at least one pharmaceutically acceptable carrier.

Compound I, Compound I Form A, a deuterated derivative of Compound I, and/or a pharmaceutically acceptable salt of Compound I or deuterated derivative thereof can be administered in a single pharmaceutical composition or separate pharmaceutical compositions. Such pharmaceutical compositions can be formulated for once daily administration (i.e., every 24 hours (q24h)) or multiple administrations daily, such as twice daily or three times daily.

In some embodiments, Compound I, a deuterated derivative of Compound I, and/or a pharmaceutically acceptable salt of Compound I or deuterated derivative thereof is administered in combination with one or more other therapeutic agents. In some embodiments, the other therapeutic agent(s) is selected from an angiotensin converting enzyme (ACE) inhibitor, an angiotensin receptor blocker (ARB), a neprilysin inhibitor, a sodium-glucose co-transporter-2 (SGLT2) inhibitor, a renin inhibitor, an immunosuppressant such as, e.g., tacrolimus, mycophenolate, cyclosporine, or a systemic corticosteroid, such as, e.g., prednisone or prednisone equivalent, and a mineralocorticoid receptor antagonist. In some embodiments, the other therapeutic agent(s) is selected from an angiotensin converting enzyme (ACE) inhibitor, an angiotensin receptor blocker (ARB), a sodium glucose co-transporter 2 (SGLT2) inhibitor, a renin inhibitor, a neprilysin inhibitor, and a systemic corticosteroid (e.g., prednisone or a prednisone equivalent). In certain embodiments, Compound I, a deuterated derivative of Compound I, and/or a pharmaceutically acceptable salt of Compound I or its deuterated derivative is administered in combination with an ACE inhibitor (ACEi) and an ARB. In certain embodiments, Compound I, a deuterated derivative of Compound I, and/or a pharmaceutically acceptable salt of Compound I or its deuterated derivative is administered in combination with an ACE inhibitor (ACEi), an ARB, and prednisone or a prednisone equivalent.

As used herein, the term "angiotensin-converting enzyme inhibitor" or "ACE inhibitor" refers to a class of medications, such as a small molecule organic chemistry compounds ($\leq 1$ kDa) or a large biomolecule such as a peptide (e.g., a soluble peptide), protein (e.g., an antibody), nucleic acid (e.g., siRNA) or a conjugate combining any two or more of the foregoing, that blocks the formation of a natural chemical angiotensin I that narrows blood vessels, to thereby cause relaxation of blood vessels as well as a decrease in blood, which leads to lower blood pressure and decreased oxygen demand from the heart. Non-limiting examples of ACE inhibitors include lisinopril (Prinivil®, Zestril®, Qbrelis®), combinations of lisinopril with hydrochlorothiazide (Zestoretic®), benazepril (Lotensin®), captopril (Capoten®), enalapril (Vasotec®, Renitec®, Epaned®, Enacard®), zofenopril, perindopril (Aceon®), trandopril (Mavik®), quinapril (Accupril®), and ramipril (Altace®).

As used herein, the term "angiotensin receptor blocker" or "ARB" refers to a class of medications, such as a substance, such as a small molecule organic chemistry compounds ($\leq 1$ kDa) or a large biomolecule such as a peptide (e.g., a soluble peptide), protein (e.g., an antibody), nucleic acid (e.g., siRNA) or a conjugate combining any two or more of the foregoing, that blocks the action (not formation as it is with ACE inhibitors) of angiotensin I that narrows blood vessels, to thereby cause relaxation of blood vessels as well as a decrease in blood, which leads to lower blood pressure and decreased oxygen demand from the heart. Non-limiting examples of ARBs include losartan (Cozaar®), irbesartan (Avapro®), olmesartan (Benicar®), telmisartan (Micardis®), candesartan (Atacand®), valsartan (Diovan®), fimasartan, azilsartan (Edarbi®), erposartan, and iosartan potassium-hydrochloridethiazide (Hyzaar®).

As used herein, the term "renin inhibitor" refers to a class of medications, such as a substance, such as a small molecule organic chemistry compounds ($\leq 1$ kDa) or a large biomolecule such as a peptide (such as, e.g., a soluble peptide), protein (such as, e.g., an antibody), nucleic acid (such as, e.g., an siRNA) or a conjugate combining any two or more of the foregoing, that slows down the production of renin, an enzyme produced by the kidneys that starts a chain of reactions that increase blood pressure, including the production of angiotensin I. The first approved drug in this class is aliskiren (Tekturna®). Due to a risk of serious complications, including stroke, aliskiren cannot be taken without an ACE inhibitor or an ARB.

As used herein, the term "neprilysin inhibitor" refers to a class of medications, such as a substance, such as a small molecule organic chemistry compounds ($\leq 1$ kDa) or a large biomolecule such as a peptide (e.g., a soluble peptide), protein (e.g., an antibody), nucleic acid (e.g., siRNA) or a conjugate combining any two or more of the foregoing, that prevents neprilysin's activity against signaling peptides such as enkephalins, substance P, endothelin, antrial natriuretic peptide. Neprilysin is expressed in many types of tissues but is particularly abundant in the kidneys, and is a zinc-dependent metalloprotease that cleaves and inactivates several peptide hormones including glucagon, enkephalins, substance P, neurotensin, oxytocin, and bradykinin. Non-limiting examples of neprilysin inhibitors include sacubitril/valsartan (Entresto®/LCZ696), sacubitril (AHU-377), sacubitrilat (LBQ657), RB-101, UK-414, UK-495, omapatrilat, ecadotril, and candoxatril.

As used herein, the term "sodium glucose co-transporter 2 inhibitor" or "SGLT2 inhibitor" refers to a class of medications, such as a substance, such as a small molecule organic chemistry compounds ($\leq 1$ kDa) or a large biomolecule such as a peptide (e.g., a soluble peptide), protein (e.g., an antibody), nucleic acid (e.g., siRNA) or a conjugate combining any two or more of the foregoing, that possesses the activity of inhibiting sodium-glucose transport protein 2 (SGLT2). Non-limiting examples of SGLT2 inhibitors include empagliflozin (Jardiance®), canagliflozin (Invokana®), dapagliflozin (Farxiga®), remogliflozin (including remogliflozin etabonate BHV091009_, ipragliflozin IASP-1941 or Suglat®), HM41322, bexagliflozin, ertugliflozin (Steglatro®), sotagliflozin, luseogliflozin, tofogliflozin (Apleway®, Beberza®), sergliflozin etabonate or a pharmaceutically acceptable salt of any of the foregoing. Additional examples of SGLT2 inhibitors are disclosed in WO01/027128, WO04/013118, WO04/080990, EP1852439A1, WO01/27128, WO03/099836, WO2005/092877, WO2006/034489, WO2006/064033, WO2006/117359, WO2006/117360, WO2007/025943, WO2007/028814, WO2007/031548, WO2007/093610, WO2007/128749, WO2008/049923, WO2008/055870, and WO2008/055940, each of which is incorporated herein by reference in its entirety.

As used herein, the term "systemic corticosteroid" refers to a corticosteroid that is administered orally or by injection, and does not include corticosteroids used in the eyes, ears, or nose, and on the skin. Non-limiting examples of a systemic corticosteroid include prednisone or a prednisone equivalent (e.g., prednisolone, methylprednisolone), beclomethasone, betamethasone, dexamethasone, hydrocortisone, and triamcinolone.

As used herein, the term "mineralocorticoid receptor antagonist" to a class of medications, such as a substance, such as a small molecule organic chemistry compounds (≤1 kDa) or a large biomolecule such as a peptide (e.g., a soluble peptide), protein (e.g., an antibody), nucleic acid (e.g., siRNA) or a conjugate combining any two or more of the foregoing, that possesses the activity of antagonizing the action of aldosterone (a mineralocorticoid) at mineralocorticoid receptors. Small molecule mineralocorticoid receptor antagonists may be steroidal or nonsteroidal compounds and may be spirolactones with the structural feature of a cyclic ester attached spiro to another ring system. Non-limiting examples of mineralocorticoid receptor antagonists include spironolactone, eplerenone, canrenone, finerenone, and mexrenone.

In some embodiments, the disclosure provides a pharmaceutical composition comprising 2 mg to 250 mg of Compound I, Compound I Form A, a deuterated derivative of Compound I, and/or a pharmaceutically acceptable salt of Compound I or its deuterated derivative, and at least one pharmaceutically acceptable carrier. In some embodiments, the pharmaceutical composition comprising 2 mg to 250 mg, 5 mg to 200 mg, 10 mg to 150 mg, 15 mg to 100 mg, 20 mg to 80 mg, 25 to 75 mg, 30 to 60 mg, or 15 mg to 45 mg of Compound I, Compound I Form A, a deuterated derivative of Compound I, and/or a pharmaceutically acceptable salt of Compound I or deuterated derivative thereof, and at least one pharmaceutically acceptable carrier. In some embodiments, the disclosure provides a pharmaceutical composition comprising 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg of Compound I, a deuterated derivative of Compound I, Compound I Form A, and/or a pharmaceutically acceptable salt of Compound I or its deuterated derivative, and optionally at least one pharmaceutically acceptable carrier. In some embodiments, the disclosure provides a pharmaceutical composition comprising 15 mg, 20 mg, 25 mg, 30 mg, 35 mg, 40 mg, 45 mg, 50 mg, 55 mg, or 60 mg of Compound I, Compound I Form A, a deuterated derivative of Compound I, and/or a pharmaceutically acceptable salt of Compound I or its deuterated derivative, and at least one pharmaceutically acceptable carrier.

In some embodiments, the disclosure provides a pharmaceutical composition comprising 15 mg of Compound I, a deuterated derivative of Compound I, and/or a pharmaceutically acceptable salt of Compound I or its deuterated derivative, and at least one pharmaceutically acceptable carrier. In some embodiments, the disclosure provides a pharmaceutical composition comprising 30 mg of Compound I, a deuterated derivative of Compound I, and/or a pharmaceutically acceptable salt of Compound I or its deuterated derivative, and at least one pharmaceutically acceptable carrier. In some embodiments, the disclosure provides a pharmaceutical composition comprising 45 mg of Compound I, a deuterated derivative of Compound I, and/or a pharmaceutically acceptable salt of Compound I or its deuterated derivative, and at least one pharmaceutically acceptable carrier. In some embodiments, the disclosure provides a pharmaceutical composition comprising 60 mg of Compound I, a deuterated derivative of Compound I, and/or a pharmaceutically acceptable salt of Compound I or its deuterated derivative, and at least one pharmaceutically acceptable carrier. In some embodiments, the disclosure provides a pharmaceutical composition comprising 75 mg of Compound I, a deuterated derivative of Compound I, and/or a pharmaceutically acceptable salt of Compound I or its deuterated derivative, and at least one pharmaceutically acceptable carrier.

In some embodiments, the disclosure provides a pharmaceutical composition comprising 15 mg of Compound I Form A and at least one pharmaceutically acceptable carrier. In some embodiments, the disclosure provides a pharmaceutical composition comprising 30 mg of Compound I Form A and at least one pharmaceutically acceptable carrier. In some embodiments, the disclosure provides a pharmaceutical composition comprising 45 mg of Compound I Form A and at least one pharmaceutically acceptable carrier. In some embodiments, the disclosure provides a pharmaceutical composition comprising 60 mg of Compound I Form A and at least one pharmaceutically acceptable carrier. In some embodiments, the disclosure provides a pharmaceutical composition comprising 75 mg of Compound I Form A and at least one pharmaceutically acceptable carrier.

In some embodiments, the patient receiving Compound I, Compound I Form A, a deuterated derivative of Compound 1, and/or a pharmaceutically acceptable salt of Compound I or its deuterated derivative or a pharmaceutical composition comprising the same is administered is in the fasted state. As used herein, a patient who is in the "fasted state" has abstained from all food and drink (except water) for at least two hours (such as for at least four hours) before and at least two hours after administration of Compound I, a deuterated derivative of Compound I, and/or a pharmaceutically acceptable salt of Compound I or its deuterated derivative or a pharmaceutical composition comprising the same.

In some embodiments, the patient to whom Compound I, Compound I Form A, a deuterated derivative of Compound I, and/or a pharmaceutically acceptable salt of Compound I or its deuterated derivative or a pharmaceutical composition comprising the same is administered is in the fed state. As used herein, a patient who is in the "fed state" has abstained from all food and drink (except water) for at least eight hours (such as for at least ten hours) before the start of a meal and consumption of the meal is started within 30 minutes of administration of Compound I, a deuterated derivative of Compound I, and/or a pharmaceutically acceptable salt of Compound I or its deuterated derivative or a pharmaceutical composition comprising the same and the entire meal is consumed in 30 minutes or less. In some embodiments, additional food is not permitted for at least two hours (such as four hours) after administration of Compound I, a deuterated derivative of Compound I, and/or a pharmaceutically acceptable salt of Compound I or its deuterated derivative or a pharmaceutical composition comprising the same. In some embodiments, water may be consumed without restriction beginning after administration of Compound I, a deuterated derivative of Compound I, and/or a pharmaceutically acceptable salt of Compound I or its deuterated derivative or a pharmaceutical composition comprising the same. In some embodiments, water may be consumed without restriction beginning at least one hour after administration. In some embodiments, the meal is a high-fat meal, such as a meal containing about 800-1000 calories total and containing about 500-600 calories from fat and/or 55-65 grams of fat. In some embodiments, the meal is a low-fat meal, such as a meal containing about 500-600 calories total and containing about 100-125 calories from fat and/or 11-14 grams of fat. In some embodiments, the meal is a moderate-fat meal, such as a meal containing about 500-600 calories total and containing about 30-35% fat and/or about 20 g of fat.

A pharmaceutical composition comprising Compound I, Compound I Form A, a deuterated derivative of Compound I, and/or a pharmaceutically acceptable salt of Compound I or its deuterated derivative, may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

The "at least one pharmaceutically acceptable carrier," as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

The pharmaceutical compositions described herein are useful for treating APOL1 mediated disease, including APOL1-mediated kidney disease, e.g., FSGS and/or NDKD. In some embodiments, the pharmaceutical compositions described herein are useful for treating APOL1-mediated kidney disease. In some embodiments, the pharmaceutical compositions described herein are useful for treating FSGS. In some embodiments, the pharmaceutical compositions described herein are useful for treating NDKD.

Any suitable pharmaceutical formulation known in the art can be used for compositions comprising Compound I, Compound I Form A, a deuterated derivative of Compound I, and/or a pharmaceutically acceptable salt of Compound I or its deuterated derivative. In some embodiments, the pharmaceutical compositions employed in the therapies of the disclosure are tablets. In some embodiments, the tablets are suitable for oral administration.

In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative and cellulose. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative and croscarmellose sodium. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative and sodium stearyl fumarate. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative and lactose monohydrate. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative and hypromellose acetate succinate. In some embodiments, pharmaceutical compositions of the disclosure (including, but not limited to, tablets) comprise I, Compound I Form A, a deuterated derivative of Compound I, and/or a pharmaceutically acceptable salt of Compound I or its deuterated derivative, cellulose, and croscarmellose sodium. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative, cellulose, croscarmellose sodium, and lactose monohydrate. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative, cellulose, croscarmellose sodium, hypromellose acetate succinate, and lactose monohydrate. In some embodiments, pharmaceutical compositions of the disclosure (including, but not limited to, tablets) comprise Compound I, Compound I Form A, a deuterated derivative of Compound I, and/or a pharmaceutically acceptable salt of Compound I or its deuterated derivative, cellulose, croscarmellose sodium, lactose monohydrate, hypromellose acetate succinate, and sodium stearyl fumarate.

In some embodiments, a tablet comprising Compound I, Compound I Form A, a deuterated derivative of Compound I, and/or a pharmaceutically acceptable salt of Compound I or its deuterated derivative may optionally further comprise a coating. In some embodiments, a tablet comprising Compound I, Compound I Form A, a deuterated derivative of Compound I, and/or a pharmaceutically acceptable salt of Compound I or its deuterated derivative further comprises a coating comprising polyvinyl alcohol (PVA), polyethylene glycol (PEG), titanium dioxide, and talc, which is referred to herein as a "non-functional film coating." An exemplary embodiment of a tablet comprising 250 mg of Compound I, a deuterated derivative of Compound I, Compound I Form A, a deuterated derivative of Compound I, and/or a pharmaceutically acceptable salt of Compound I or its deuterated derivative and further comprising a non-functional film coating is shown in Table 2. The non-functional film coating can be applied to the tablet comprising Compound I, Compound I Form A, a deuterated derivative of Compound I, and/or a pharmaceutically acceptable salt of Compound I or its deuterated derivative using traditional tablet film coating processes.

TABLE 2

Exemplary Tablet Comprising 15 mg of Compound I and a Film Coating.

| Component | Component Function | Content (% w/w) | Amount per Tablet (mg) |
|---|---|---|---|
| Compound I | Active | 15.00 | 15.00 |
| Microcrystalline Cellulose | Diluent | 78.50 | 78.50 |
| Croscarmellose Sodium | Disintegrant | 3.90 | 3.90 |
| Sodium Stearyl fumarate | Lubricant | 2.60 | 2.60 |
| Total | — | 100.00 | 100.00 |

In some embodiments, disclosed herein are methods of treating, lessening the severity of, or symptomatically treating an APOL1-mediated disease, including an APOL1-mediated kidney disease such as FSGS and/or NDKD in a patient comprising administering an effective amount of Compound I, Compound I Form A, a deuterated derivative of Compound I, and/or a pharmaceutically acceptable salt of Compound I or its deuterated derivative; or a pharmaceutical composition comprising Compound I, Compound I Form A, a deuterated derivative of Compound I, and/or a pharmaceutically acceptable salt of Compound I or its deuterated derivative as disclosed herein to a patient suffering from FSGS or NDKD.

Non-limiting embodiments of the disclosure include:
1. A method of treating APOL1-mediated disease comprising administering to a patient in need thereof Compound I:

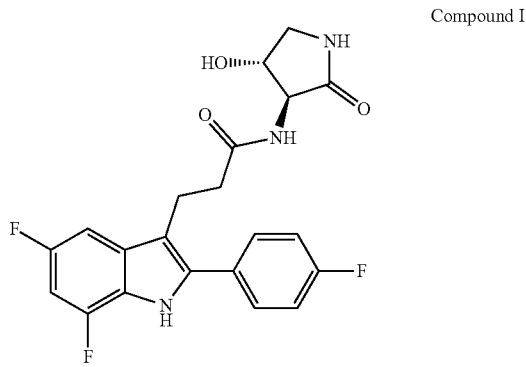 [SMILES: O=C(CCc1c(-c2ccc(F)cc2)[nH]c2c(F)cc(F)cc12)N[C@@H]1C(=O)NC[C@H]1O]

Compound I a deuterated derivative thereof, and/or a pharmaceutically acceptable salt of Compound I or deuterated derivative thereof and in a daily amount of 2 mg to 100 mg.
2. The method of embodiment 1, wherein the APOL1-mediated disease is APOL1 mediated kidney disease.
3. The method of embodiment 2, wherein the APOL1-mediated kidney disease is APOL1-dependent focal segmental glomerulosclerosis (FSGS).
4. The method of embodiment 2, wherein the APOL1-mediated kidney disease is non-diabetic kidney disease (NDKD).
5. The method according to any one of embodiments 1-4, wherein the patient has an APOL1 genotype.
6. The method according to any one of embodiments 1-4, wherein the patient has nephrotic range proteinuria.
7. The method according to any one of embodiments 1-4, wherein the patient does not have nephrotic range proteinuria.
8. The method according to any one of embodiments 1-7, wherein Compound I, a deuterated derivative thereof, and/or a pharmaceutically acceptable salt of Compound I or deuterated derivative thereof is administered in a daily amount of 5 mg to 200 mg, 10 mg to 150 mg, 15 mg to 100 mg, 20 mg to 80 mg, 25 to 75 mg, 30 to 60 mg, or 15 mg to 45 mg.
9. The method according to any one of embodiments 1-7, wherein Compound I, a deuterated derivative thereof, and/or a pharmaceutically acceptable salt of Compound I or deuterated derivative thereof is administered in a daily amount of 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg.
10. The method according to any one of embodiments 1-9, wherein Compound I, a deuterated derivative thereof, and/or a pharmaceutically acceptable salt of Compound I or deuterated derivative thereof is administered in a daily amount of 15 mg, or 45 mg.
11. The method according to any one of embodiments 1-10, wherein Compound I, a deuterated derivative thereof, and/or a pharmaceutically acceptable salt of Compound I or deuterated derivative thereof is administered once daily or multiple times daily.
12. The method according to any one of embodiments 1-10, wherein Compound I, a deuterated derivative thereof, and/or a pharmaceutically acceptable salt of Compound I or deuterated derivative thereof is administered every 24 hours (q24h).
13. The method according to any one of embodiments 1-12, wherein the method comprises administering Compound I or a deuterated derivative thereof.
14. The method according to any one of embodiments 1-12, wherein the method comprises administering a pharmaceutically acceptable salt of Compound I or a deuterated derivative thereof.
15. The method according to any one of embodiments 1-14, wherein the Compound I, a deuterated derivative thereof, and/or a pharmaceutically acceptable salt of Compound I or deuterated derivative thereof is comprised in a pharmaceutical composition.
16. The method according to embodiment 15, wherein the pharmaceutical composition is a tablet.
17. The method according to embodiment 16, wherein the tablet is suitable for oral administration.
18. The method according to embodiment 17, wherein the tablet for oral administration comprises 15 mg of Compound I.
19. The method according to any one of embodiments 16-18, wherein the tablet comprises cellulose, croscarmellose sodium, and/or sodium stearyl fumarate.

20. The method according to embodiment 19, wherein the tablet further comprises a coating comprising polyvinyl alcohol (PVA), polyethylene glycol (PEG), titanium dioxide, and talc.
21. The method according to any one of embodiments 1-20, wherein the patient is in the fasted state.
22. The method according to any one of embodiments 1-20, wherein the patient is in the fed state.
23. The method according to any one of embodiments 1-22, wherein Compound I, a deuterated derivative thereof, and/or a pharmaceutically acceptable salt of Compound I or deuterated derivative thereof is administered in combination with one or more therapeutic agents selected from an angiotensin converting enzyme (ACE) inhibitor, an angiotensin receptor blocker (ARB), a sodium-glucose co-transporter-2 (SGLT2) inhibitor, a renin inhibitor, a neprilysin inhibitor, an immunosuppressant, and a mineralocorticoid receptor antagonist.
23(a). The method according to embodiment 23, wherein the immunosuppressant is selected from tacrolimus, cyclosporine, mycophenolate, and a systemic corticosteroid.
24. The method according to embodiment 23(a), wherein the systemic corticosteroid is prednisone or a prednisone equivalent.
25. The method according to any one of embodiments 1-22, wherein Compound I, a deuterated derivative thereof, and/or a pharmaceutically acceptable salt of Compound I or deuterated derivative thereof is administered in combination with one or more therapeutic agents selected from an angiotensin converting enzyme (ACE) inhibitor, an angiotensin receptor blocker (ARB), a renin inhibitor, and a prednisone equivalent.
26. The method according to any one of embodiments 1-22, wherein Compound I, a deuterated derivative thereof, and/or a pharmaceutically acceptable salt of Compound I or deuterated derivative thereof is administered in combination with an ACE inhibitor (ACEi) and an ARB.
27. The method according to any one of embodiments 1-22, wherein Compound I, a deuterated derivative thereof, and/or a pharmaceutically acceptable salt of Compound I or deuterated derivative thereof is administered in combination with an ACEi, an ARB, and prednisone.
28. The method according to any one of embodiments 1-27, wherein the patient is not co-administered with any immunosuppressant other than a systemic corticosteroid, tacrolimus, cyclosporine, and mycophenolate.
29. The method of any one of embodiments 1-28, wherein Compound I is substantially pure crystalline Form A.
30. The method of any one of embodiments 1-28, wherein Compound I is crystalline Form A.
31. A pharmaceutical composition comprising 5 mg to 200 mg, 10 mg to 150 mg, 15 mg to 100 mg, 20 mg to 80 mg, 25 to 75 mg, 30 to 60 mg, or 15 mg to 45 mg Compound I, a deuterated derivative thereof, and/or a pharmaceutically acceptable salt of Compound I or deuterated derivative thereof.
32. The pharmaceutical composition according to embodiment 31, wherein the composition comprises 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg of Compound I, a deuterated derivative thereof, and/or a pharmaceutically acceptable salt of Compound I or deuterated derivative thereof.
33. The pharmaceutical composition according to embodiment 32, wherein the composition comprises 15 mg of Compound I.
34. The pharmaceutical composition according to embodiment 32, wherein the composition comprises 30 mg of Compound I.
35. The pharmaceutical composition according to embodiment 32, wherein the composition comprises 45 mg of Compound I.
36. The pharmaceutical composition according to embodiment 32, wherein the composition comprises 60 mg of Compound I.
37. The pharmaceutical composition according to embodiment 32, wherein the composition comprises 75 mg of Compound I.
38. The pharmaceutical composition of any one of embodiments 31 to 37, wherein Compound I is substantially pure crystalline Form A.
39. The pharmaceutical composition of any one of embodiments 31 to 37, wherein Compound I is crystalline Form A.

Example 1: Synthesis of Compound I

Part A: Synthesis of Starting Materials

Preparation S2

(3S,4R)-3-amino-4-hydroxy-pyrrolidin-2-one (S2)

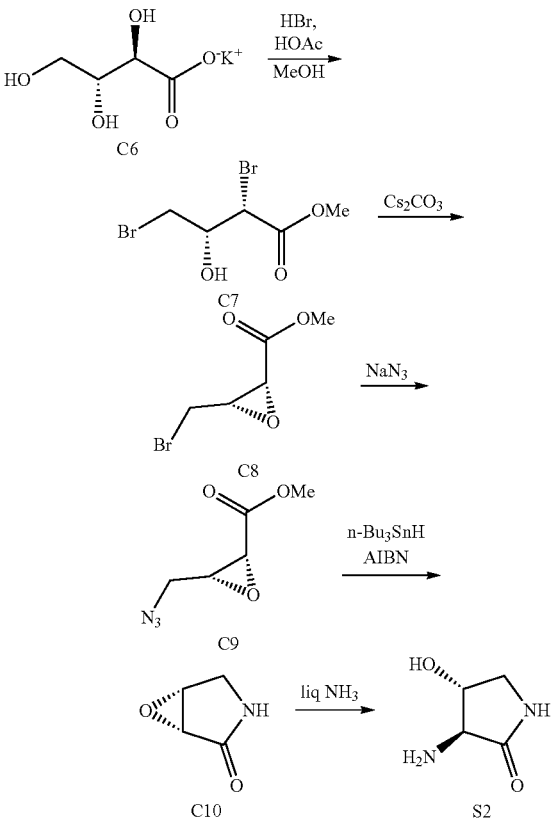

Step 1. Synthesis of methyl (2S,3R)-2,4-dibromo-3-hydroxy-butanoate (C7)

Potassium (2R,3R)-2,3,4-trihydroxybutanoate C6 (10 g, 57.1 mmol) was stirred with HBr in Acetic acid (154 g, 103 mL of 30% w/w, 570.8 mmol) for 16 h. Anhydrous MeOH (250 mL) was added and the mixture heated at reflux for 4 h. The mixture was concentrated dryness and the residue dissolved in EtOAc (100 mL). The solution was washed with water (50 mL) and brine (50 mL), then dried over $Na_2SO_4$, and concentrated in vacuo. Purification by silica gel chromatography (Gradient: 15-20% EtOAc in hexane) afforded the product as a colorless liquid (13 g, 83%). $^1$H NMR (400 MHz, $CDCl_3$) δ 4.71 (d, J=3.4 Hz, 1H), 4.17-4.14 (m, 1H), 3.82 (s, 3H), 3.53-3.44 (m, 2H).

Step 1. Alternative Procedure for Synthesis of Methyl (2S,3R)-2,4-dibromo-3-hydroxy-butanoate (C7)

Potassium (2R,3R)-2,3,4-trihydroxybutanoate C6 (280 g) was stirred with a 33% solution of HBr in acetic acid (1 L) at room temperature for 24 h. The reaction mixture was then poured into MeOH (5 L). The mixture was stirred at room temperature for 8 h, then at 65° C. for 4 h. The mixture was concentrated, the residue was dissolved in MeOH (1.2 L) and then concentrated sulfuric acid (30 mL) was slowly added. The mixture was heated under reflux for 6 h, then concentrated. The residue was taken up with EtOAc (400 mL). The resulting solution was washed with water (250 mL), dried over $Na_2SO_4$, filtered and concentrated in vacuo to give the product as an oil which solidified upon storage at 4° C. (375 g, 74%).

Step 2. Synthesis of Methyl (2R,3S)-3-(bromomethyl)oxirane-2-carboxylate (C8)

Methyl (2R,3R)-2,4-dibromo-3-hydroxy-butanoate C7 (524.8 g, 1.9 mol) was dissolved in acetone (4.5 L) in a 12 L round-bottomed flask equipped with an overhead stirrer. The reaction was cooled to 0° C. in an ice-bath and $Cs_2CO_3$ (994 g, 3.1 mol) was added. The reaction was stirred for 30 minutes at 0° C. and then for 2 h at room temperature. The mixture was filtered, washing with acetone, and then concentrated in vacuo to afford a dark grey oil residue. The product was dissolved in $CH_2Cl_2$ and filtered over a short plug of silica gel, eluting with $CH_2Cl_2$ (approx. 1 L). The filtrate was concentrated in vacuo to afford the product as a clear yellow oil (377.3 g, quantitative). $^1$H NMR (300 MHz, $CDCl_3$) δ 3.83 (s, 3H), 3.71-3.61 (m, 2H), 3.61-3.53 (m, 1H), 3.46 (dd, J=9.9, 6.6 Hz, 1H) ppm. $^{13}$C NMR (75 MHz, $CDCl_3$) δ 167.58, 55.89, 53.52, 52.77, 26.83 ppm.

Step 2. Alternative Procedure for Synthesis of Methyl (2R,3S)-3-(bromomethyl)oxirane-2-carboxylate (C8)

To a solution of methyl (2R,3R)-2,4-dibromo-3-hydroxy-butanoate C7 (200 g, 0.73 mol) in acetone (2.0 L) was added anhydrous $K_2CO_3$ (151.1 g, 1.1 mol), while the reaction temperature was maintained at 0-5° C. The reaction was stirred at 0-5° C. for 2 h, then gradually warmed to room temperature over 4 h The reaction mixture was filtered and the filtrate was concentrated under reduced pressure. The residue was distilled under vacuum 75-80° C./200-300 Pa to give the product as a colorless liquid (105 g, 74%).

Step 3. Synthesis of Methyl (2R,3R)-3-(azidomethyl)oxirane-2-carboxylate (C9)

Methyl (2R,3S)-3-(bromomethyl)oxirane-2-carboxylate C8 (52.6 g, 269.7 mmol) was dissolved in DMF (500 mL) in a 3 L round-bottomed flask equipped with a magnetic stir bar. $NaN_3$ (25.3 g, 388.4 mmol) was added and the mixture was stirred at room temperature for 1 h. The reaction was poured into water, and extracted with EtOAc. The extract was washed with water, dried over $MgSO_4$, and concentrated in vacuo to afford a dark red oil. The oil residue was dissolved in $CH_2Cl_2$, and filtered over a plug of silica gel eluting with $CH_2Cl_2$. The filtrate was concentrated in vacuo to afford the product as a clear, light red oil (40.8 g, 96%). $^1$H NMR (300 MHz, $CDCl_3$) δ 3.87-3.74 (m, 3H), 3.67-3.55 (m, 2H), 3.47 (dd, J=13.3, 5.1 Hz, 1H), 3.38 (ddd, J=6.3, 5.0, 4.4 Hz, 1H). $^{13}$C NMR (75 MHz, $CDCl_3$) δ 167.76, 54.81, 52.67, 51.32, 48.74.

Step 4. Synthesis of (1R,5R)-6-oxa-3-azabicyclo [3.1.0]hexan-2-one (C10)

A 2 L 3-neck flask with overhead stirrer was charged with methyl (2R,3R)-3-(azidomethyl)oxirane-2-carboxylate C9 (67 g, 402.5 mmol) in toluene (500 mL), stirred for 10 minutes, and then warmed to 80° C. $Bu_3SnH$ (220 mL, 817.8 mmol) and AIBN (2 g, 12.2 mmol) were dissolved in toluene (500 mL) and then added to the reaction over 3 h using an additional funnel. The resulting reaction mixture was stirred at 80-87° C. for 1 h, then cooled to ambient temperature, and concentrated under reduced pressure. The residue was partitioned between acetonitrile (2 L) and pentane (1 L), stirred for 10 minutes and then the acetonitrile phase (bottom) was separated. The acetonitrile phase was washed with pentane (2×500 mL) and concentrated in vacuo to afford a light yellow solid. The solid residue was triturated with pentane (~200 mL) to afford the product as a yellow solid which was used without further purification (52 g, 98%). $^1$H NMR (300 MHz, $CDCl_3$) δ 5.89 (s, 1H), 4.00 (q, J=2.5 Hz, 1H), 3.74-3.50 (m, 2H), 3.44 (dd, J=12.4, 2.4 Hz, 1H). $^{13}$C NMR (75 MHz, $CDCl_3$) δ 173.24, 53.28, 52.18, 44.00.

Step 5. Synthesis of (3S,4R)-3-amino-4-hydroxy-pyrrolidin-2-one (S2)

A parr vessel containing (1R,5R)-6-oxa-3-azabicyclo [3.1.0]hexan-2-one C10 (60 g, 605.5 mmol) and NH3 (1.5 L, 58.6 mol) was pressurized to 200 psi and allowed to stir at 18° C. for 2 days. NH3 was released from the vessel to provide a grey solid. Heptane was added and the mixture stirred for 30 min. The solid was filtered, and then the filter cake was isolated, and then EtOAc and heptane to the solid. The mixture was concentrated in vacuo to afford the product (55 g, 78%). $^1$H NMR (300 MHz, $D_2O$) δ 4.13 (q, J=7.2 Hz, 1H), 3.53 (dd, J=10.4, 7.4 Hz, 1H), 3.36 (d, J=7.5 Hz, 1H), 3.05 (dd, J=10.4, 6.8 Hz, 1H).

Alternative Preparation S2

(3S,4R)-3-amino-4-hydroxypyrrolidin-2-one hydrochloride (S2)

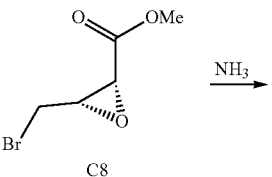

-continued

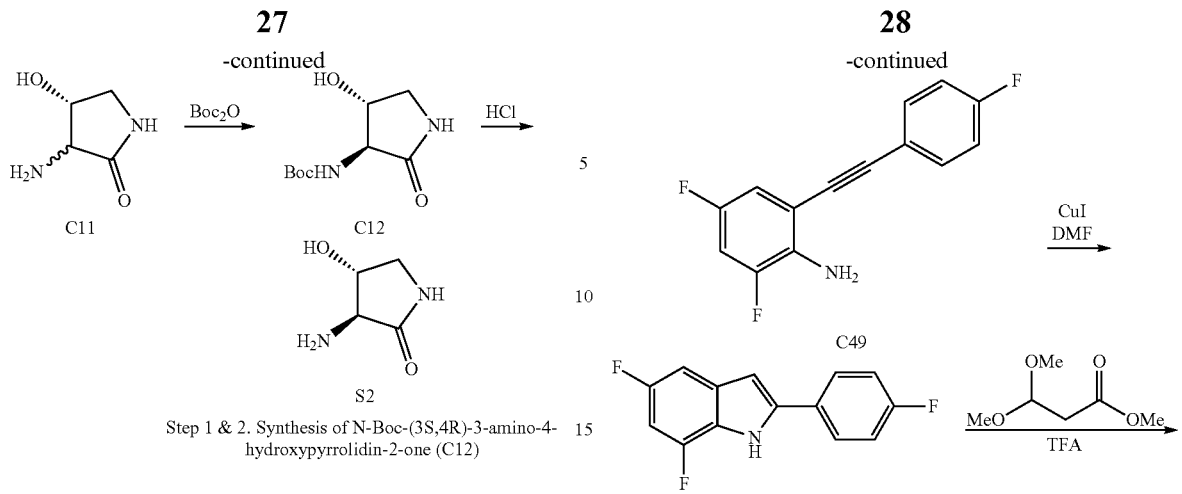

Step 1 & 2. Synthesis of N-Boc-(3S,4R)-3-amino-4-hydroxypyrrolidin-2-one (C12)

At −60° C., ammonia gas was condensed into an autoclave containing a frozen solution of methyl (2R,3 S)-3-(bromomethyl)oxirane-2-carboxylate C8 (81 g, 0.42 mol) in 1,4-dioxane (160 mL) until approx. 400 mL of liquid was collected. The autoclave was closed, allowed to warm gradually to room temperature and then heated at 50-60° C. for 2 h. The autoclave was then cooled back to −60° C. and depressurized. The reaction mixture was warmed gradually to allow the liquid ammonia to evaporate, leaving a viscous residue. The residue was taken up with MeOH (500 mL) and the suspension was treated with a 28% solution of sodium methoxide in MeOH (86 g, 0.42 mol). The mixture was stirred at room temperature for 30 min then concentrated. The residue was dissolved in water (500 mL), then $Na_2CO_3$ (89 g, 0.84 mol) and a solution of $Boc_2O$ (110 g, 0.5 mol) in THF (200 mL) was added. The mixture was stirred at room temperature for 10 h. The aqueous phase was then saturated with NaCl, and extracted THF (3×200 mL). The combined organic phases were dried over $Na_2SO_4$ and concentrated in vacuo. The residue was triturated with warm MTBE (200 mL) and the precipitated solid was collected by filtration, washed with MTBE and dried under vacuum to afford the product as a white solid (28 g, 31% yield).

Step 3. Synthesis of (3S,4R)-3-amino-4-hydroxypyrrolidin-2-one hydrochloride (S2)

To solution of N-Boc-(3S,4R)-3-amino-4-hydroxypyrrolidin-2-one C12 (28 g, 129 mmol) in EtOH (300 mL) heated at 50-60° C. was added a solution of HCl in EtOH (5.0 M, 75 mL). The reaction mixture was kept at 50-60° C. for 2 h. The suspension was cooled to room temperature and the solid was collected by filtration, washed with EtOH and dried in vacuo to afford the product as an off-white solid (18 g, 90%). $^1$H NMR (500 MHz, DMSO-$d_6$) δ 8.73 (brs, 3H), 8.28 (s, 1H), 6.03 (s, 1H), 4.42-4.37 (m, 1H), 3.74 (d, J=6.8 Hz, 1H), 3.48-3.39 (m, 1H), 3.03-3.00 (m, 1H).

Preparation S12

(3-[5,7-difluoro-2-(4-fluorophenyl)-1H-indol-3-yl]propanoic acid (S12)

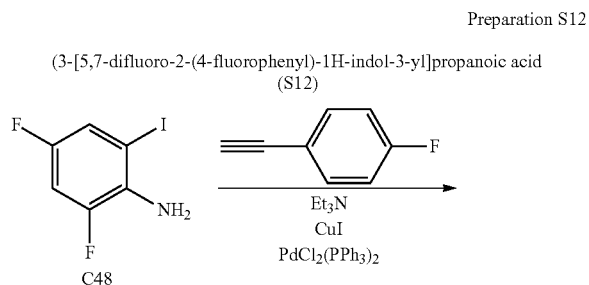

Step 1. Synthesis of 2,4-difluoro-6-[2-(4-fluorophenyl)ethynyl] aniline (C49)

Method A: Sonagashira Coupling Method. To a flask containing 2,4-difluoro-6-iodo-aniline C48 (134 g, 525.5 mmol) was added $NEt_3$ (1.3 L), followed by DMF (250 mL), 1-ethynyl-4-fluoro-benzene (83.5 g, 695.1 mmol), CuI (20.5 g, 107.6 mmol), and $PdCl_2(PPh_3)_2$ (25 g, 35.6 mmol). The mixture was allowed to stir at room temperature for 2 h. Solvent was removed under reduced pressure and water (500 mL) was added. The mixture was extracted with Ethyl acetate, filtered and concentrated in vacuo. The product mixture was filtered through a silica gel plug (Eluent: $CH_2Cl_2$), followed by a second silica plug filtration (Eluent: 30-40% EtOAc in Heptane). Silica gel chromatography (Gradient: 0-20% EtOAc in heptane) afforded the product as a pale yellow solid. (87 g, 60%). $^1$H NMR (300 MHz, CDCl$_3$) δ 7.58-7.45 (m, 2H), 7.14-7.02 (m, 2H), 6.92 (ddd, J=8.8, 2.8, 1.7 Hz, 1H), 6.87-6.71 (m, 1H), 4.15 (s, 2H). LCMS m/z 248.0 [M+H]$^+$.

Step 2. Synthesis of 5,7-difluoro-2-(4-fluorophenyl)-1H-indole (C50)

Method B: Amine-Alkyne cyclization Method (CuI promoted). To a solution of 2,4-difluoro-6-[2-(4-fluorophenyl)ethynyl]aniline C49 (46 g, 167.5 mmol) in DMF (600 mL) was added CuI (1.9 g, 10.0 mmol) and the reaction was heated at reflux. Water (800 mL) was added and the mixture extracted with MTBE. The mixture was then washed with sat. NaCl solution, dried over Na$_2$SO$_4$ and then concentrated in vacuo to afford the product, which was used in subsequent steps without further purification (41 g, 87%). $^1$H NMR (300 MHz, CDCl$_3$) δ 8.43 (s, 1H), 7.72-7.58 (m, 2H), 7.27-7.15 (m, 2H), 7.09 (dd, J=9.0, 2.1 Hz, 1H), 6.85-6.63 (m, 2H). LCMS m/z 248.0 [M+H]$^+$.

Step 3. Synthesis of Methyl (E)-3-[5,7-difluoro-2-(4-fluorophenyl)-1H-indol-3-yl]prop-2-enoate (C51)

Method C: Reductive Alkylation Method (TFA promoted). A 12 L flask with overhead stirrer was charged with 5,7-difluoro-2-(4-fluorophenyl)-1H-indole C50 (300 g, 1.2 mol), CH$_2$Cl$_2$ (3 L), methyl 3,3-dimethoxypropanoate (195 mL, 1.4 mol) and TFA (300 mL, 3.9 mol). The reaction was heated to reflux for 4 h. Additional CH$_2$Cl$_2$ was added to facilitate stirring. Upon cooling to room temperature, the solid product was filtered, washed with minimal CH$_2$Cl$_2$ and dried to afford the product (388 g, 96%). $^1$H NMR (400 MHz, DMSO-d$_6$) δ 12.66 (s, 1H), 7.77-7.57 (m, 4H), 7.56-7.37 (m, 2H), 7.19 (ddd, J=11.0, 9.7, 2.1 Hz, 1H), 6.47 (d, J=16.1 Hz, 1H), 3.69 (s, 3H). LCMS m/z 332.4 [M+H]$^+$.

Step 4. Synthesis of Methyl 3-[5,7-difluoro-2-(4-fluorophenyl)-1H-indol-3-yl]propanoate (C52)

Method D: Pd(OH)$_2$ Catalyzed Transfer Hydrogenation. To a suspension of methyl (E)-3-[5,7-difluoro-2-(4-fluorophenyl)-1H-indol-3-yl]prop-2-enoate C51 (80 g, 236.5 mmol) in EtOH (1.5 L) under a nitrogen atmosphere was added Pd(OH)$_2$ (6 g of 20% w/w 8.5 mmol) and ammonium formate (160 g, 2.5 mol). The mixture was heated at reflux for ~3 h, then filtered to remove catalyst. The filtrate was concentrated in vacuo to afford the product as an off-white solid which was used without further purification (82 g, 100%). $^1$H NMR (300 MHz, CDCl$_3$) δ 8.18 (s, 1H), 7.65-7.47 (m, 2H), 7.27-7.14 (m, 2H), 7.14-7.00 (m, 1H), 6.76 (ddd, J=10.8, 9.4, 2.2 Hz, 1H), 3.65 (s, 3H), 3.27-3.04 (m, 2H), 2.75-2.49 (m, 2H). LCMS m/z 334.3 [M+H]$^+$.

Step 5. Synthesis of 3-[5,7-difluoro-2-(4-fluorophenyl)-1H-indol-3-yl]propanoic acid (S12)

Method E: Ester hydrolysis with LiOH. LiOH (67 g, 2.8 mol) was added to a solution of methyl 3-[5,7-difluoro-2-(4-fluorophenyl)-1H-indol-3-yl]propanoate C52 (217 g, 651.1 mmol) in THF (1 L) and water (100 mL). The mixture was heated at reflux for 2 h, and then allowed to cool overnight. THF was removed by concentration under reduced pressure, and water was added (approx. 1 L). The mixture was cooled on an ice bath and HCl (250 mL of 11.7 M, 2.9 mol) was added to adjust pH to ~4. EtOAc (300 mL) was added, and the aqueous layer extracted with further EtOAc (100 mL). Combined organic extracts were dried over sodium sulfate (Na$_2$SO$_4$), filtered through a plug of silica gel rinsing with EtOAc. The filtrate was concentrated in vacuo to afford an orange oil (50-75 mL). Heptanes (~50 mL) were added and the mixture chilled on dry ice. Upon agitation, a crystalline solid formed. The mixture was allowed to stir on an ice-bath until to allow completion of the crystallization process. The solid was filtered, washed with heptane and air dried to afford the product (208 g, 96%). $^1$H NMR (300 MHz, CDCl$_3$) δ 8.15 (s, 1H), 7.60-7.46 (m, 2H), 7.27-7.15 (m, 2H), 7.09 (dd, J=9.1, 2.2 Hz, 1H), 6.77 (ddd, J=10.8, 9.4, 2.2 Hz, 1H), 3.26-3.05 (m, 2H), 2.78-2.57 (m, 2H). LCMS m/z 320.0 [M+H]$^+$.

Alternative Preparation S12

Step 3. Synthesis of Methyl (E)-3-[5,7-difluoro-2-(4-fluorophenyl)-1H-indol-3-yl]prop-2-enoate (C51)

A reactor was charged with 5,7-difluoro-2-(4-fluorophenyl)-1H-indole C50 (4.0 kg, 16.5 mol), CH$_2$Cl$_2$ (37 L) and methyl 3,3-dimethoxypropanoate (2.6 L, 18.1 mol) followed by TFA (3.9 L, 51.0 mol) at ambient temperature. The resulting mixture was heated to reflux for 6 h. The batch was then cooled to 20° C., charged with n-heptane (2 vol) and filtered. The filter cake was dried under vacuum at 45° C. to afford the product in ~90% yield. $^1$H NMR (300 MHz, DMSO-d$_6$) δ 12.63 (s, 1H), 7.76-7.54 (m, 4H), 7.55-7.39 (m, 2H), 7.18 (ddd, J=11.1, 9.7, 2.2 Hz, 1H), 6.46 (d, J=16.1 Hz, 1H), 3.69 (s, 3H). LCMS m/z 332.1 [M+H]$^+$.

Step 4. Synthesis of Methyl 3-[5,7-difluoro-2-(4-fluorophenyl)-1H-indol-3-yl]propanoate (C52)

Methyl (E)-3-[5,7-difluoro-2-(4-fluorophenyl)-1H-indol-3-yl]prop-2-enoate C51 (1.5 kg, 9.06 mol) was slurried with THF (7 L) in a vessel. Pd(OH)$_2$ (10 g of 20% w/w, ~50% water, 0.014 mol) was charged. The mixture was purged with N2 three times, then once with H$_2$ and the vessel pressurized to 50 psi with H$_2$. The mixture was agitated at 20° C. until H$_2$ uptake ceased. After 1.5 h, the mixture was purged with N2 (×3) and filtered through Solka-Floc using a THF (2 vol) rinse. The resulting filtrate was concentrated in vacuo at 45° C. (to 1.5 vol), charged with cyclohexane (1 vol), and concentrated again (to 1.5 vol) at 45° C. The slurry was cooled to 15-20° C. and filtered. The filter cake was then washed with cold cyclohexane (1 vol), and dried under vacuum at 45° C. to afford the product in 95% yield.

Step 5. Synthesis of 3-[5,7-difluoro-2-(4-fluorophenyl)-1H-indol-3-yl]propanoic acid (S12)

A mixture of methyl 3-[5,7-difluoro-2-(4-fluorophenyl)-1H-indol-3-yl]propanoate C52 (9 kg, 27 mmol) in 2-MeTHF (54 L, 6 vol) and MeOH (8.1 L, 0.9 vol) was charged with 20% KOH (2 equiv, 54 mol). The mixture was stirred at 35° C. for 6 h. The mixture was then distilled under vacuum to 27 L (3 vol) and cooled to 10-15° C. Water (7.5 L) and 2-MeTHF (16 L) were charged and the resulting biphasic mixture was pH adjusted with 6 M HCl to a pH ~2. The temperature was adjusted to 20° C. and the phases separated. The organic phase was washed with water (15 L), filtered through Celite® with 2-MeTHF rinse (18 L, 2 vol), and concentrated under vacuum to 18 L (2 vol). 18 L (2 vol) of n-heptane was charged and the batch again concentrated under vacuum to 18 L (3 vol). This cycle was repeated once more and the batch was seeded. 16 L (1.8 vol) n-heptane was charged and the temperature adjusted to 20° C. The slurry was stirred for 2 h, filtered and the cake washed with 2×18 L (2×2 vol) n-heptane. The filter cake was dried under vacuum at 45° C. to afford the desired product in 90% yield. $^1$H NMR (300 MHz, CDCl$_3$) δ 8.28 (s, 1H), 7.53 (ddd, J=8.7, 5.4, 2.8 Hz, 2H), 7.27-7.13 (m, 2H), 7.08 (dd, J=9.1, 2.1 Hz, 1H), 6.76 (ddd, J=11.3, 9.4, 2.2 Hz, 1H), 3.91-3.69 (m, 4H), 3.28-3.07 (m, 2H), 2.79-2.53 (m, 2H), 2.00-1.74 (m, 3H). LCMS m/z 320.4 [M+H]$^+$.

Part B: Synthesis of Compound (I)

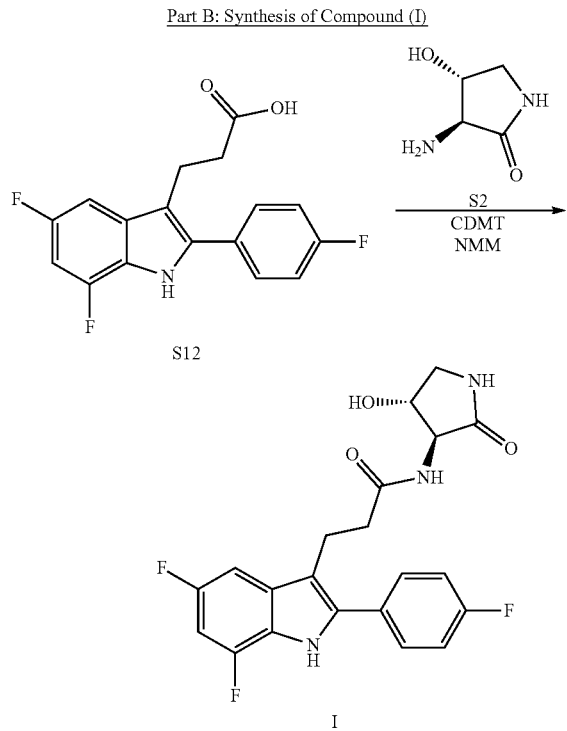

Synthesis of 3-[5,7-difluoro-2-(4-fluorophenyl)-1H-indol-3-yl]-N-[(3S,4R)-4-hydroxy-2-oxo-pyrrolidin-3-yl]propanamide (I)

A 2 L 3-neck RB flask with magnetic stirrer, temperature probe and nitrogen inlet was charged with 3-[5,7-difluoro-2-(4-fluorophenyl)-1H-indol-3-yl]propanoic acid S12 (90.5 g, 283.5 mmol) and (3S,4R)-3-amino-4-hydroxy-pyrrolidin-2-one S2 (39.9 g, 343.6 mmol) in DMF (1.65 L), and stirred for 15 minutes. CDMT (61.1 g, 348 mmol) was added. The mixture was then cooled to ~2° C. on an ice bath. N-methylmorpholine was added (131 mL, 1.2 mol) dropwise over 20 minutes and the mixture was heated at 30° C. overnight. The reaction mixture was added into approx. 4.5 L of ice water, and extracted with EtOAc (1.2 L×4). The combined organic layers, were washed with 1.2 L of 1 M HCl (×3) and then water (1.2 L) and brine (1.2 L). The combined organic layers were dried over Na$_2$SO$_4$, filtered and concentrated. The mixture was washed through a silica gel plug (1.8 L of silica gel), first eluting with 25% EtOAc in dichloromethane (8 L) to remove impurities, followed by hot EtOAc (8 L), to elute the product. The EtOAc filtrate was concentrated in vacuo. TBME was then added (400 mL), and the mixture allowed to stir overnight. Filtration of the resulting solid afforded the product as a white solid. 62 g, 52%) $^1$H NMR (300 MHz, CD$_3$OD) δ 7.70-7.58 (m, 2H), 7.29-7.13 (m, 3H), 6.73 (ddd, J=11.1, 9.6, 2.2 Hz, 1H), 4.34 (td, J=7.6, 6.8 Hz, 1H), 4.21 (d, J=7.8 Hz, 1H), 3.56 (dd, J=9.9, 7.6 Hz, 1H), 3.20-3.04 (m, 3H), 2.65-2.53 (m, 2H). LCMS m/z 418.2 [M+H]$^+$.
Optical rotation: $[\alpha]_D^{20.7}$=−14.01 (c=1.0, 10 mg in 1 mL of MeOH).

Alternative Procedure for Synthesis of Compound I

Step 1. Synthesis of Methyl (E)-3-[5,7-difluoro-2-(4-fluorophenyl)-1H-indol-3-yl]prop-2-enoate (C51)

A solution of 5,7-difluoro-2-(4-fluorophenyl)-1H-indole C50 (100 g, 1.0 equiv) in dichloromethane (850 mL, 8.5 vol) was agitated at 22° C. Methyl 3,3-dimethoxypropionate (63 mL, 1.1 equiv) was charged followed by trifluoroacetic acid (96 mL, 3.1 equiv), which was rinsed forward with dichloromethane (25 mL, 0.25 vol). The batch was heated to 38° C. and stirred at that temperature. After 4h, the batch was cooled to 22° C. and charged with n-heptane (200 mL, 2 vol). The mixture was stirred for no less than 1 h at 22° C. The slurry was filtered, and the reactor and the filter cake were washed with n-heptane (1×2 vol (200 mL) and 1×3 vol (300 mL)). The resulting solid was dried under vacuum with nitrogen bleed at 45° C. to afford the product C51 (127.7 g, 95% yield).

Step 2. Synthesis of Methyl 3-[5,7-difluoro-2-(4-fluorophenyl)-1H-indol-3-yl]propanoate (C52)

To a hydrogenator was charged methyl (E)-3-[5,7-difluoro-2-(4-fluorophenyl)-1H-indol-3-yl]prop-2-enoate C51 (100.4 g, 1.0 equiv) followed by Pd(OH)$_2$/C (0.014 equiv). The vessel was sealed and three vacuum/purge cycles with N2 were performed. 2-MeTHF (2000 mL, 20 vol) was charged using residual vacuum and the resulting mixture was stirred at 22° C. The vessel was sealed and three vacuum/purge cycles with N2 were performed followed by one vacuum purge cycle with hydrogen (H$_2$). The temperature was adjusted to 22° C., and the vessel pressurized with 20 psi H$_2$. The mixture was agitated at 22° C. for 4 h. Three vacuum/purge cycles with nitrogen N2 were performed. The batch was filtered through a pad of Hyflo® and the filter cake was rinsed with 2-MeTHF (2×300 mL, 2×3 vol). The combined filtrates were placed under vacuum and distilled at ≤45.0° C. to 2.0 to 3.0 total volumes. The batch temperature was adjusted to 22° C. and the vessel was charge with n-heptane (1000 mL, 10 vol) over at least 1 h. A vacuum was applied and the filtrate distilled at ≤45.0° C. to 3.5 to 4.5 total volumes. The slurry was cooled to 22° C. and allowed to stir for no less than 1 h. The slurry was filtered and the filter cake was washed with n-heptane (1×1 vol (100 mL) and 1×0.5 vol (50 mL)). The solids were dried under vacuum with nitrogen bleed at 45° C. to afford the product C52 (91.9 g, 91% yield).

Step 3. Synthesis of 3-[5,7-difluoro-2-(4-fluorophenyl)-1H-indol-3-yl]propanoic acid (S12)

A mixture of methyl 3-[5,7-difluoro-2-(4-fluorophenyl)-1H-indol-3-yl]propanoate C52 (80.0 g, 1.0 equiv) and 2-MeTHF (480 mL, 6 vol) was agitated at 22° C. and treated with methanol (72 mL, 0.9 vol). A solution of KOH (27.1 g, 2.0 equiv) in water (107 mL, 1.3 vol) was charged over approximately 20 min. The resulting mixture was heated to an internal temperature of 35° C. and stirred for 3 h. The temperature was adjusted to 22° C. A vacuum was applied and the mixture was distilled at ≤45° C. to 3.0 total volumes. The internal temperature was adjusted to 12° C. The mixture was then charged with water (64 mL, 0.8 vol) and 2-MeTHF (304 mL, 3.8 vol). 6 N HCl (75 mL, 0.9 vol) was slowly charged into the mixture with vigorous agitation until the batch attained a pH<3. The internal temperature was adjusted to 22° C., and the biphasic mixture was stirred for no less than 0.5 h. The stirring was stopped and the phases were allowed to separate for no less than 0.5 h. The lower aqueous phase was removed. Water (160 mL, 2 vol) was charged to the reactor at 22° C., and the biphasic mixture stirred for no less than 0.5 h. The stirring was stopped, and the phases allowed separated over no less than 0.5 h. The lower aqueous phase was removed and the batch was filtered through a pad of Hyflo®. The reactor and filter cake were rinsed with 2-MeTHF (160 mL, 2 vol). A vacuum was applied and the combined filtrates distilled at ≤40.0° C. to 2-3 total volumes. The vessel was charged with n-heptane (160 mL, 2 vol), a vacuum was applied and the filtrate distilled at ≤40.0° C. to 2 total volumes (this step was repeated one additional time). The mixture was then charged with additional n-heptane (144 mL, 1.8 vol). The internal temperature was adjusted to 40° C. and stirred for no less than 2 h. The internal temperature was adjusted to 22° C. over a minimum of 5 h and stirred for no less than 16 hours. The slurry was filtered. The filter cake was washed with n-heptane (3×40 mL, 3×0.5 vol). The solids were dried under vacuum with nitrogen bleed at 45° C. to afford product S12 (72.6 g, 95% yield).

Step 4. Synthesis of 3-[5,7-difluoro-2-(4-fluorophenyl)-1H-indol-3-yl]-N-[(3S,4R)-4-hydroxy-2-oxopyrrolidin-3-yl]propanamide (Compound I)

A mixture of S12 (50.0 g, 1.0 equiv), (3S,4R)-3-amino-4-hydroxypyrrolidin-2-one hydrochloride S2 (25.1 g, 1.05 equiv), and CDMT (30.3 g, 1.1 equiv) in DMF (250 mL, 5 vol) was agitated and cooled to 0° C. The reactor was charged with NMM (60 mL, 3.5 equiv) over no less than 1 h, while maintaining the internal temperature at ≤5° C. The batch was stirred at ~5° C. for no less than 1 h. The batch was warmed to 22° C. over at least 1 h and stirred at 22° C. for 16 h. The batch was cooled to 0° C. Water (250 mL, 5 vol) was charged, while keeping the internal temperature <20° C. The mixture was charged with a 90/10 mixture of EtOAc/IPA (1000 mL, 20 vol). 6 N HCl (40 mL, 0.8 vol) was then charged, while maintaining an internal temperature <10° C., until a pH ~1-3 was achieved. The internal temperature was adjusted to 22° C. and the biphasic mixture stirred for no less than 0.5 h. Stirring was stopped and the phases allowed to separate for no less than 0.5 h. The lower aqueous phase was removed. The aqueous layer was back extracted with a 90/10 mixture of EtOAc/IPA (2×250 mL, 2×5 vol) at 22° C. The combined organic phases from extractions were washed with water (5×500 mL, 5×10 vol) at 22° C., by mixing for no less than 0.5 h and settling for no less than 0.5 h for each wash. The batch was polish filtered. A vacuum was applied and the organic phase distilled at <50° C. to 9.5-10.5 total volumes. The mixture was charged with EtOAc (500 mL, 10 vol), vacuum was applied and the organic phase distilled at <50° C. to 9.5-10.5 total volumes (this step was repeated one more time). The mixture was charged with EtOAc (300 mL, 6 vol) and n-heptane (200 mL, 4 vol). The resulting slurry was heated to 50° C. and stirred for no less than 17 h. The mixture was then cooled to 22° C. over 2 h, and stirred for no less than 1 h. The slurry was filtered. The filter cake was washed with 1:1 EtOAc/n-heptane (2×150 mL, 2×3 vol). The solids were dried under vacuum with nitrogen bleed at ≤45° C. to afford Compound I (52.6 g, 80% yield).

Re-Crystallization of Compound I

Compound 2 (37.6 g, 1.0 equiv) was charged to a reactor followed by a 3:1 mixture of IPA/water (240 mL, 6.4 vol). The slurry was heated to an internal temperature of 75° C. The batch was cooled to an internal temperature of 55° C. and stirred at that temperature for at least 0.5 h. The batch was seeded with 0.5 wt % of a previously generated batch of Compound 2, as a suspension in a mixture of 3:1 IPA/water (4 mL, 0.1 vol). The mixture was stirred at 55° C. for no less than 1.5 h. Water (218 mL, 5.8 vol) was added over minimum period of 5 h while maintaining the temperature at 55° C. The slurry was cooled to 22° C. over no less than 5 h and stirred for no less than 2 h. The slurry was filtered. The filter cake was washed with 2:3 IPA/water (2×114 mL, 2×3 vol). The solids were dried under vacuum with nitrogen bleed at ≤45° C. to afford Compound I (34.5 g, 92% yield).

Compound I Form A 12.3 kg of Compound I was charged to the reactor followed by a 3:1 mixture of 2-propanol/water. Agitation was initiated and the mixture was heated to 75° C. to achieve complete dissolution. The mixture was cooled to 55° C. over 1 hour and agitated at that temperature for 30 minutes. Agitation was continued for 1.5 hours. Water (5.8 vol) was charged over 5 h at 55° C., after which the mixture was cooled to 22° C. over 6 hours. The mixture was agitated at 22° C. for 2 hours then filtered under vacuum. The resulting wet cake was washed with a 3:1 mixture of 2-propanol/water (2.74 vol×2) and pulled dry under vacuum. The wet cake was further dried under vacuum with nitrogen bleed at 45° C. to yield 11.2 kg of Form A.

X-Ray Powder Diffraction for Compound I Form A

The powder X-ray powder diffraction diffractogram of Compound I Form A (FIG. 1) was acquired at room temperature using the PANalytical Empyrean diffractometer equipped with PIXcel 1D detector. The peaks are listed in table 11 below.

TABLE 3

Peak list from powder X-ray powder diffraction diffractogram of Form A

| Angle (Degrees 2-Theta ±0.2) | Intensity % |
|---|---|
| 26.3 | 100.0 |
| 13.2 | 76.6 |
| 9.5 | 53.9 |
| 26.7 | 40.9 |
| 19.8 | 38.7 |
| 14.4 | 32.5 |
| 19.2 | 30.5 |
| 28.6 | 25.0 |
| 19.5 | 23.5 |
| 18.8 | 22.3 |
| 20.7 | 21.2 |
| 21.4 | 17.7 |
| 17.7 | 17.6 |
| 24.0 | 16.7 |
| 22.9 | 16.4 |
| 21.7 | 15.7 |
| 27.7 | 12.7 |
| 27.1 | 12.4 |
| 16.1 | 12.0 |
| 29.1 | 11.0 |
| 29.5 | 10.4 |
| 23.3 | 10.3 |
| 22.4 | 10.1 |

Solid State NMR of Compound I Form A

Figure 2:
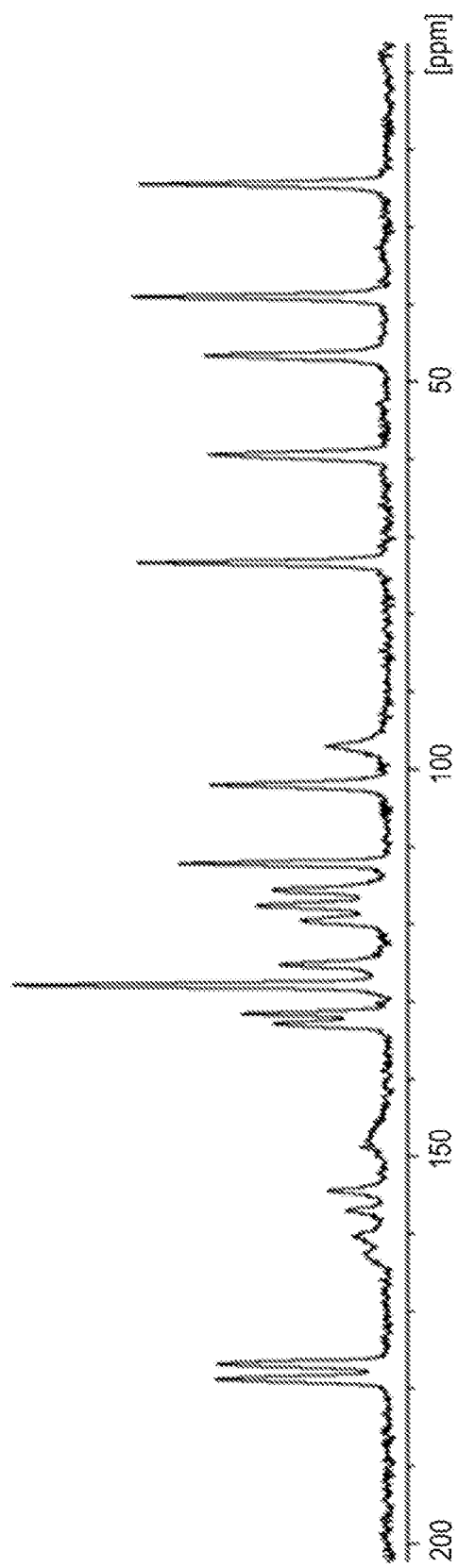
FIG. 2 depicts a solid state $^{13}C$ NMR spectrum for Compound I Form A.

The $^{13}$C CPMAS of Compound I Form A (FIG. 2) was acquired at 275 K with the following parameters: 12.5 kHz spinning; ref. adamantane 29.5 ppm. The peaks are listed in table 12 below. The carbon peaks highlighted in bold are unique for Form A with respect to following forms: Hydrate A, Hydrate C and amorphous form.

TABLE 4

Peak list from $^{13}$C CPMAS of Form A

| Chem Shift [ppm] | Intensity [rel] |
|---|---|
| 178.7 | 46.1 |
| 176.7 | 46 |
| 162.5 | 6.6 |
| 160.3 | 9.6 |
| 157.0 | 11.4 |
| 154.4 | 16.2 |
| 148.8 | 7.6 |
| 132.8 | 30.8 |
| 131.5 | 39.0 |
| 127.8 | 100.0 |
| 125.2 | 28.7 |
| 119.4 | 23.3 |
| 117.5 | 35.0 |
| 115.5 | 30.8 |
| 112.1 | 55.8 |
| 102.0 | 47.5 |
| 97.0 | 16.7 |
| 73.3 | 67.0 |
| 59.3 | 48.0 |
| 46.6 | 49.1 |
| 38.9 | 68.3 |
| 24.4 | 66.5 |

Example 3: Preparation of a Coated Tablet Containing 15 mg of Compound I

The following materials can be used in this exemplary preparation of a tablet containing 15 mg of Compound I, as shown in Table 3.

TABLE 5

Exemplary Tablet Comprising 15 mg of Compound I.

| Material | % W/W Core Tablet | Tablet Quantity (mg) |
|---|---|---|
| Compound I (Form A) | 15.00 | 15.00 |
| Microcrystalline Cellulose, NF Avicel PH-101 (Intragranular) | 61.00 | 61.00 |
| Croscarmellose Sodium, Ac-Di-Sol, NF(Intragranular) | 2.40 | 2.40 |
| Sodium Stearyl fumarate, NF (Intragranular)$^a$ | 1.60 | 1.60 |
| Microcrystalline Cellulose, Avicel PH-102 (Extragranular) | 17.50 | 17.50 |
| Croscarmellose Sodium, Ac-Di-Sol, NF (Extragranular) | 1.50 | 1.50 |
| Sodium stearyl fumarate, NF (Extragranular)$^a$ | 1.00 | 1.00 |
| TOTAL | 100.00 | 100.00 |

In this exemplary preparation, Compound I and the intragranular microcrystalline cellulose and croscarmellose sodium are sieved, combined in a bin blender, and blended. Sieved intragranular sodium stearyl fumarate is added to the bin blender, and the mixture is blended. The mixture is then dry granulated and milled to form milled granules. These milled granules are added to a bin blender, to which sieved extragranular microcrystalline cellulose and sieved extragranular croscarmellose sodium are then added. The mixture es blended. Sieved extragranular sodium stearyl fumarate is added to the bin blender, and the mixture is blended. The resulting blend is discharged and then charged to a tablet press. The blend is compressed into tablets, which are then discharged. The non-functional film coating is optionally applied to the tablet comprising Compound I using traditional tablet film coating processes.

Example 4: Efficacy of Compound I for Treating APOL1-Mediated Focal Segmental Glomerulosclerosis Inclusion Criteria for a Phase 2, open-label, single-arm, 2-part study of Compound 1. Participants are between the ages of 18 and 65 years, inclusive;
2. Participants have a body mass index (BMI) of 18.0 to 40.0 kg/m$^2$, inclusive, and a total body weight >50 kg;
3. Participants are diagnosed with FSGS by kidney biopsy, with the exception of the tip variant, as confirmed through the Eligibility Review Process;
4. Participants have an APOL1 genotype of G1/G1, G2/G2, or G1/G2 obtained with a clinical study assay, which may be confirmed by Sanger Sequencing;
5. Participants have a UPCR ratio of ≥3 g/g and <10 g/g (Cohort 1) or a UPCR ratio of ≥1 g/g and <2.7 g/g (Cohort 2) in the first morning void on 3 measurements collected on at least 3 separate days, within a 7-day period, during the Screening Period (all 3 measurements must meet this criterion);
6. Participants have an estimated glomerular filtration rate (eGFR≥45 mL/min/1.73 m$^2$ (Cohort 1) or an eGFR≥30 mL/min/1.73 m$^2$ (Cohort 2) based on the Chronic Kidney Disease Epidemiology Collaboration (CKD-EPI) equation; Participants with an eGFR≥30 to <40 mL/min/1.73 m$^2$ must have tubulointerstitial fibrosis ≤50% or described as no, mild, or moderate on the kidney biopsy (Cohort 2); and
7. Participants have no plan to start, stop, or modify dosing for an angiotensin converting enzyme (ACE) inhibitor, angiotensin receptor blocker (ARB), neprilysin inhibitor, sodium-glucose co-transporter-2 (SGLT2) inhibitor, renin inhibitor, systemic corticosteroids, tacrolimus, or mycophenolate from 28 days before Screening through the Follow-up Period.
8. Participants who are on low-dose corticosteroids (≤10 mg/day of predisone or prednisone equivalent) or on an allowed immunosuppressant (e.g. tacrolimus or mycophenolate) must be on a stable dose for 28 days before screening.

The clinical trial contains two cohorts. Cohort 1 and Cohort 2 are permitted to take a stable low dose of systemic corticosteroids (≤10 mg/day of predisone or prednisone equivalent), tacrolimus and mycophenolate, but other immunosuppressants are not permitted. The objectives and dosing schedules of Cohort 1 and Cohort 2 are identical.

Initially, participants undergo screening assessments during a 28-day Screening Period and provide informed consent. Screening assessments include, but are not limited to, analysis of vital signs, height and weight, electrocardiographic measurements, serum chemistry, UPCR (urine protein to creatinine ratio), and the like. The risk-allele status (APOL1 genotype) is assessed at any time prior to initiation of treatment (e.g., during the screening period).

All participants receive a dose of 15 mg q24h for 2 weeks and a dose of 45 mg q24h for 11 weeks thereafter. After the last dose, participants are followed for up to 12 weeks for evaluation of proteinuria off treatment. Participants who prematurely discontinue taking Compound I are scheduled for an early treatment termination visit as soon as possible after the decision to terminate study drug treatment; these participants continue to complete all other scheduled study visits for assessments of efficacy (i.e., UPCR (urine protein to creatinine ratio), UACR (urine albumin to creatinine ratio)) until completion of the last follow-up visit. After the last dose of study drug, participants are followed monthly for up to 12 weeks or until UPCR returns to baseline, whichever occurs first. All subjects complete a safety follow-up visit at 28 (±7) days after the last dose of study drug.

Proteinuria is assessed at multiple timepoints throughout the treatment and follow-up periods. Timepoints for primary analysis are day 1 and week 13.

The study participants include male and female subjects with a diagnosis of FSGS with a confirmed APOLI genotype. Participants receive 15 mg q24h doses of Compound I for 2 weeks and 45 mg q24h doses of Compound I for 11 weeks.

The primary endpoint to assess the effect on FSGS is the percent change from baseline in UPCR at Week 13. As used herein, "baseline value" is the most recent measurement (scheduled or unscheduled) collected before the first dose of study drug. For ECGs, the baseline value is defined as the average of the pretreatment measurements (triplicate) before the first dose of Compound I. "Change (absolute change) from baseline" is calculated as post-baseline value minus baseline value. "Relative change from baseline" is calculated and expressed in percentage as 100%×(post-baseline value minus baseline value)/baseline value.

Example 5: Efficacy of Compound I for Treating APOL1-Mediated Nondiabetic Kidney Disease Inclusion Criteria for a Phase 2, double-blind, placebo-controlled, dose-ranging study of Compound I:
1. Participants are between the ages of 18 and 60 years, inclusive;
2. Participants have a body mass index (BMI) of 18.0 to 40.0 kg/m', inclusive, and a total body weight >50 kg;
3. Participants have an APOLI genotype of G1/G1, G2/G2, or G1/G2 obtained with a clinical study assay;
4. Participants have a UPCR ratio of ≥0.2 g/g and <3 g/g in the first morning void on 3 measurements collected on at least 3 separate days, within a 7-day period, during the Screening Period (all 3 measurements must meet this criterion);
5. Participants have a glomerular filtration rate (GFR)≥30 mL/min/1.73 m² based on the Chronic Kidney Disease Epidemiology Collaboration (CKD-EPI) equation; and
6. Participants have no plan to start, stop, or modify dosing for an angiotensin converting enzyme (ACE) inhibitor, an angiotensin receptor blocker (ARB) neprilysin inhibitor, sodium-glucose co-transporter-2 (SGLT2) inhibitor, or renin inhibitor during the Treatment Period.
7. Participants with a history of hypertension and currently on a stable dose (at least 4 weeks) of antihypertensive medications.

Initially, participants undergo screening assessments during a 28-day Screening Period and provide informed consent. Screening assessments include, but are not limited to, analysis of vital signs, height and weight, electrocardiographic measurements, serum chemistry, UPCR (urine protein to creatinine ratio), and the like. The risk-allele status (APOL1 genotype) is assessed at any time prior to initiation of treatment (e.g., during the screening period).

The participants will be randomized to receive a dose of Compound I or placebo. Participants will receive a low dose, mid dose, or high dose of Compound I for 13 weeks thereafter. Compound I doses will be determined before the study start using available data from clinical and nonclinical studies. Participants who prematurely discontinue taking Compound I are scheduled for an early treatment termination visit as soon as possible after the decision to terminate study drug treatment; these participants continue to complete all other scheduled study visits for assessments of efficacy (i.e., UPCR (urine protein to creatinine ratio), UACR (urine albumin to creatinine ratio)) until completion of the last follow-up visit. All subjects complete a safety follow-up visit at 28 (±7) days after the last dose of study drug.

Proteinuria is assessed at multiple timepoints throughout the treatment and follow-up periods. Timepoints for primary analysis are day 1 and week 13.

The study participants include male and female subjects with a confirmed APOL1 genotype and no diabetes/autoimmune induced nephropathy. Participants receive placebo or low, mid, or high doses of Compound I for 13 weeks.

The primary endpoint to assess the effect on APOL1-mediated Nondiabetic Kidney Disease is the percent change from baseline in UPCR at Week 13. As used herein, "baseline value" is the average of the 3 screening UPCR values used to determine eligibility. The primary analysis will be based on a mixed-effects model for repeated measures (MMRM) with change from baseline as the dependent variable.

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:
1. A method of treating APOL1-mediated kidney disease comprising administering to a patient in need thereof one or more compound(s) selected from:
(a) Compound I:

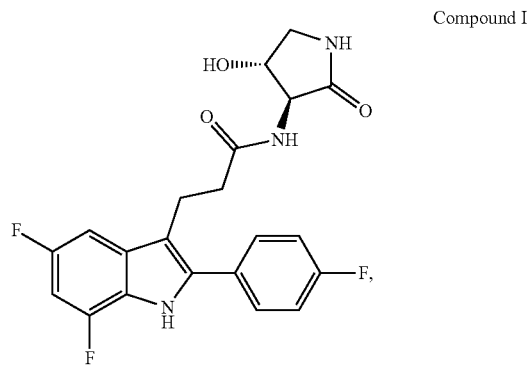 [SMILES: O=C(CCc1c(-c2ccc(F)cc2)[nH]c2c(F)cc(F)cc12)N[C@@H]1C(=O)NC[C@H]1O]

(b) a deuterated derivative of Compound I,
(c) a pharmaceutically acceptable salt of Compound I, and
(d) a pharmaceutically acceptable salt of a deuterated derivative of Compound I in a daily amount equivalent to 2 mg to 250 mg of Compound I.

2. The method of claim 1, wherein the APOL1-mediated kidney disease is APOL1-dependent focal segmental glomerulosclerosis (FSGS).

3. The method of claim 1, wherein the APOL1-mediated kidney disease is non-diabetic kidney disease (NDKD).

4. The method of claim 1, wherein the patient has an APOL1 genotype.

5. The method of claim 1, wherein the patient has nephrotic range proteinuria.

6. The method of claim 1, wherein the patient does not have nephrotic range proteinuria.

7. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered in a daily amount equivalent to 5 mg to 200 mg, 10 mg to 150 mg, 15 mg to 100 mg, 20 mg to 80 mg, 25 to 75 mg, 30 to 60 mg, or 15 mg to 45 mg of Compound I.

8. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I in a daily amount equivalent to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg of Compound I.

9. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I in a daily amount equivalent to 15 mg or 45 mg of Compound I.

10. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered once daily or multiple times daily.

11. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered every 24 hours (q24h).

12. The method of claim 1, wherein the method comprises administering Compound I or a deuterated derivative thereof.

13. The method of claim 1, wherein the method comprises administering a pharmaceutically acceptable salt of Compound I or a deuterated derivative thereof.

14. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is comprised in a pharmaceutical composition.

15. The method according to claim 14, wherein the pharmaceutical composition is in the form of a tablet.

16. The method according to claim 15, wherein the tablet is suitable for oral administration.

17. The method according to claim 16, wherein the tablet for oral administration comprises 15 mg of Compound I.

18. The method of claim 15, wherein the tablet comprises one or more additional ingredients selected from cellulose, croscarmellose sodium, and sodium stearyl fumarate.

19. The method according to claim 18, wherein the tablet further comprises a coating comprising polyvinyl alcohol (PVA), polyethylene glycol (PEG), titanium dioxide, and talc.

20. The method of claim 1, wherein the patient is in the fasted state.

21. The method of claim 1, wherein the patient is in the fed state.

22. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered in combination with one or more therapeutic agents selected from an angiotensin converting enzyme (ACE) inhibitor, an angiotensin receptor blocker (ARB), a sodium-glucose co-transporter-2 (SGLT2) inhibitor, a renin inhibitor, a neprilysin inhibitor, a systemic corticosteroid, tacrolimus, cyclosporine, mycophenolate, and a mineralocorticoid receptor antagonist.

23. The method of claim 22, wherein the systemic corticosteroid is prednisone or a prednisone equivalent.

24. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered in combination with one or more therapeutic agents selected from an angiotensin converting enzyme (ACE) inhibitor, an angiotensin receptor blocker (ARB), a renin inhibitor, and a prednisone equivalent.

25. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered in combination with an ACE inhibitor (ACEi) and an ARB.

26. The method of claim 1, wherein the one or more compound(s) selected from Compound I, a deuterated derivative of Compound I, a pharmaceutically acceptable salt of Compound I, and a pharmaceutically acceptable salt of a deuterated derivative of Compound I is administered in combination with an ACEi, an ARB, and prednisone.

27. The method of claim 1, wherein the patient is not co-administered with any immunosuppressant other than a systemic corticosteroid, tacrolimus, cyclosporine, and mycophenolate.

28. The method of claim 1, wherein Compound I is substantially pure crystalline Form A.

29. The method of claim 1, wherein Compound I is crystalline Form A.

30. A pharmaceutical composition comprising of one or more compound(s) selected from
(a) Compound I:

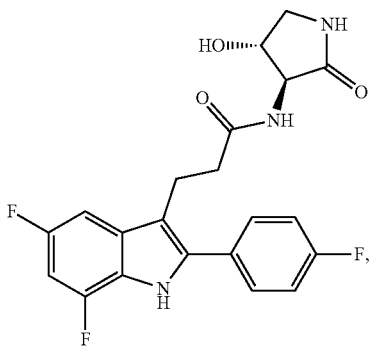

Compound I (b) a deuterated derivative thereof of Compound I,
(c) a pharmaceutically acceptable salt of Compound I, and
(d) a pharmaceutically acceptable salt of a deuterated derivative thereof of Compound I,
in an amount equivalent to 2 mg to 250 mg, 10 mg to 150 mg, 15 mg to 100 mg, 20 mg to 80 mg, 25 to 75 mg, 30 to 60 mg, or 15 mg to 45 mg of Compound I.

31. The pharmaceutical composition according to claim 30, wherein the composition comprises the one or more compound(s) selected from Compound I, a deuterated derivative of Compound I, a pharmaceutically acceptable salt of Compound I, and a pharmaceutically acceptable salt of a deuterated derivative of Compound I, in an amount equivalent to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, or 100 mg of Compound I.

32. The pharmaceutical composition according to claim 31, wherein the composition comprises 15 mg of Compound I.

33. The pharmaceutical composition according to claim 31, wherein the composition comprises 30 mg of Compound I.

34. The pharmaceutical composition according to claim 31, wherein the composition comprises 45 mg of Compound I.

35. The pharmaceutical composition according to claim 31, wherein the composition comprises 60 mg of Compound I.

36. The pharmaceutical composition according to claim 31, wherein the composition comprises 75 mg of Compound I.

37. The pharmaceutical composition of claim 30, wherein Compound I is substantially pure crystalline Form A.

38. The pharmaceutical composition of claim 30, wherein Compound I is crystalline Form A.

* * * * *